United States Patent
Hannah et al.

(10) Patent No.: US 7,838,527 B2
(45) Date of Patent: Nov. 23, 2010

(54) METHODS OF TREATING CANCER AND RELATED METHODS

(75) Inventors: Alison Hannah, Sebastopol, CA (US); Eric Harwood, Seattle, WA (US); Peter Haroldsen, Pacifica, CA (US); Carla Heise, Benecia, CA (US); Timothy Machajewski, Martinez, CA (US); Emil Samara, Danville, CA (US); Xiao Shang, Bellevue, WA (US); Jayesh Vora, Martinez, CA (US); Shuguang Zhu, Seattle, WA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1189 days.

(21) Appl. No.: 10/706,328

(22) Filed: Nov. 12, 2003

(65) Prior Publication Data

US 2004/0220196 A1 Nov. 4, 2004

Related U.S. Application Data

(60) Provisional application No. 60/460,369, filed on Apr. 3, 2003, provisional application No. 60/460,493, filed on Apr. 3, 2003, provisional application No. 60/460,328, filed on Apr. 3, 2003, provisional application No. 60/426,204, filed on Nov. 13, 2002, provisional application No. 60/426,282, filed on Nov. 13, 2002, provisional application No. 60/426,107, filed on Nov. 13, 2002, provisional application No. 60/517,915, filed on Nov. 7, 2003.

(51) Int. Cl.
A61K 31/497 (2006.01)
(52) U.S. Cl. .................. 514/255.02; 514/312
(58) Field of Classification Search ................. 544/363, 544/256.07; 514/253, 255.02, 312
See application file for complete search history.

(56) References Cited

U.S. PATENT DOCUMENTS

| | | | |
|---|---|---|---|
| 3,663,606 A | 5/1972 | Isowa | |
| 4,659,657 A | 4/1987 | Harnisch et al. | |
| 4,882,342 A | 11/1989 | Von Der Saal et al. | |
| 5,073,492 A | 12/1991 | Chen et al. | |
| 5,151,360 A | 9/1992 | Handa et al. | |
| 5,330,992 A | 7/1994 | Eissenstat et al. | |
| 5,414,088 A | 5/1995 | Von Der Saal et al. | |
| 5,480,883 A | 1/1996 | Spada et al. | |
| 5,585,380 A | 12/1996 | Bianco et al. | |
| 5,646,153 A | 7/1997 | Spada et al. | |
| 5,710,158 A | 1/1998 | Myers et al. | |
| 5,763,441 A | 6/1998 | App et al. | |
| 5,792,771 A | 8/1998 | App et al. | |
| 5,801,212 A | 9/1998 | Okamoto et al. | |
| 5,855,866 A | 1/1999 | Thorpe et al. | |
| RE36,256 E | 7/1999 | Spada et al. | |
| 5,942,385 A | 8/1999 | Hirth | |
| 5,981,569 A | 11/1999 | App et al. | |
| 6,057,320 A | 5/2000 | Spada et al. | |
| 6,111,110 A | 8/2000 | Brennan et al. | |
| 6,137,010 A | 10/2000 | Joo et al. | |
| 6,174,912 B1 | 1/2001 | Beck et al. | |
| 6,258,951 B1 | 7/2001 | Lohmann et al. | |
| 6,268,391 B1 | 7/2001 | Dickerson et al. | |
| 6,303,600 B1 | 10/2001 | Cox et al. | |
| 6,306,874 B1 | 10/2001 | Fraley et al. | |
| 6,313,138 B1 | 11/2001 | Fraley et al. | |
| RE37,650 E | 4/2002 | Myers et al. | |
| 6,420,382 B2 | 7/2002 | Fraley et al. | |
| 6,479,512 B1 | 11/2002 | Fraley et al. | |
| 6,593,344 B1 | 7/2003 | Biedermann et al. | |
| 6,605,617 B2 * | 8/2003 | Renhowe et al. | ............ 514/312 |
| 6,756,383 B2 | 6/2004 | Renhowe et al. | |
| 6,759,417 B2 | 7/2004 | Renhowe et al. | |
| 6,762,194 B2 * | 7/2004 | Renhowe et al. | ............ 514/312 |
| 6,774,237 B2 | 8/2004 | Renhowe et al. | |
| 6,774,327 B1 * | 8/2004 | Wong | ....................... 200/302.1 |
| 6,800,760 B2 * | 10/2004 | Renhowe et al. | ......... 546/270.1 |
| 7,064,215 B2 | 6/2006 | Renhowe et al. | |
| 7,179,912 B2 | 2/2007 | Halbrook et al. | |
| 7,470,709 B2 | 12/2008 | Barsanti et al. | |
| 2002/0103230 A1 | 8/2002 | Renhowe et al. | |

(Continued)

FOREIGN PATENT DOCUMENTS

AU 2003290699 6/2004

(Continued)

OTHER PUBLICATIONS

Cecil, Textbook of Medicine, 21st Edition (2000), Goldman & Bennett (Editors), W.B. Saunders Company (Publisher), Chapter 198, pp. 1060-1074).*

(Continued)

*Primary Examiner*—James D Anderson
(74) *Attorney, Agent, or Firm*—Foley & Lardner LLP

(57) ABSTRACT

Methods of treating cancer using 4-amino-5-fluoro-3-[6-(4-methylpiperazin-1-yl)-1H-benzimidazol-2-yl]quinolin-2 (1H)-one are provided. In particular, the methods are effective for the treatment of solid tumors or leukemias, including prostate, colorectal, breast, multiple myeloma, pancreatic, small cell carcinoma, acute myelogenous leukemia, chronic myelogenous leukemia, or myelo-proliferative disease. Further provided are methods of measuring the amount of 4-amino-5-fluoro-3-[6-(4-methylpiperazin-1-yl)-1H-benzimidazol-2-yl]quinolin-2(1H)-one and determining a metabolic profile therefore.

47 Claims, 2 Drawing Sheets

U.S. PATENT DOCUMENTS

| | | | |
|---|---|---|---|
| 2002/0107392 A1 | 8/2002 | Renhowe et al. | |
| 2002/0165218 A1 | 11/2002 | Halbrook et al. | |
| 2003/0028018 A1 | 2/2003 | Renhowe et al. | |
| 2003/0087854 A1 | 5/2003 | Monia et al. | |
| 2003/0158224 A1 | 8/2003 | Renhowe et al. | |
| 2003/0159702 A1* | 8/2003 | Lindell et al. | 131/270 |
| 2003/0207883 A1 | 11/2003 | Renhowe et al. | |
| 2004/0002518 A1 | 1/2004 | Renhowe et al. | |
| 2004/0006101 A1 | 1/2004 | Renhowe et al. | |
| 2004/0092535 A1 | 5/2004 | Barsanti et al. | |
| 2004/0097545 A1 | 5/2004 | Renhowe et al. | |
| 2004/0220196 A1 | 11/2004 | Hannah et al. | |
| 2005/0054672 A1 | 3/2005 | Renhowe et al. | |
| 2005/0137399 A1 | 6/2005 | Cai et al. | |
| 2005/0203101 A1 | 9/2005 | Barsanti et al. | |
| 2005/0209247 A1 | 9/2005 | Cai et al. | |
| 2005/0256157 A1 | 11/2005 | Gesner et al. | |
| 2005/0261307 A1 | 11/2005 | Cai et al. | |

FOREIGN PATENT DOCUMENTS

| | | |
|---|---|---|
| CA | 2421120 | 3/2002 |
| CL | 23463 | 11/2003 |
| DE | 2363459 | 6/1975 |
| DE | 3634066 | 4/1988 |
| DE | 19841985 | 3/2000 |
| EP | 0290153 | 11/1988 |
| EP | 0 509 717 | 4/1992 |
| EP | 0 508 800 | 10/1992 |
| EP | 0 747 771 | 12/1996 |
| EP | 0 797 376 | 9/1997 |
| EP | 0 290 153 | 11/1998 |
| EP | 1 086 705 | 3/2001 |
| HU | P0104752 | 7/2002 |
| JP | 59-130284 | 7/1984 |
| JP | 63230687 | 9/1988 |
| JP | 02-229165 | 9/1990 |
| JP | 6-99852 | 1/1994 |
| JP | 7-43896 | 2/1995 |
| JP | 8-29973 | 2/1996 |
| JP | 63-258903 | 10/1998 |
| WO | WO-91/04974 | 4/1991 |
| WO | 92/18483 | 10/1992 |
| WO | 92/20642 | 11/1992 |
| WO | WO-94/11337 | 5/1994 |
| WO | 95/15758 | 6/1995 |
| WO | 95/18801 | 7/1995 |
| WO | WO-95/18622 | 7/1995 |
| WO | 97/03069 | 1/1997 |
| WO | WO-97/21436 | 6/1997 |
| WO | 97/34876 | 9/1997 |
| WO | 97/48694 | 12/1997 |
| WO | 98/13350 | 2/1998 |
| WO | WO 98/55124 | 12/1998 |
| WO | 99/103419 | 3/1999 |
| WO | WO-99/16755 | 4/1999 |
| WO | WO-99/48868 | 9/1999 |
| WO | 99/50263 | 10/1999 |
| WO | 99/65897 | 12/1999 |
| WO | WO 00/00481 | 1/2000 |
| WO | WO 00/03990 | 1/2000 |
| WO | WO-00/11709 | 3/2000 |
| WO | WO 00/20400 | 4/2000 |
| WO | 00/27379 | 5/2000 |
| WO | WO 00/31049 | 6/2000 |
| WO | WO-00/35492 | 6/2000 |
| WO | WO 00/58315 | 10/2000 |
| WO | WO 00/71129 | 11/2000 |
| WO | WO 02/22598 A1 * | 11/2000 |
| WO | WO 00/074683 | 12/2000 |
| WO | 01/02369 | 1/2001 |
| WO | WO 01/12169 | 2/2001 |
| WO | 01/28993 | 4/2001 |
| WO | 01/29025 | 4/2001 |
| WO | WO 01/28993 | 4/2001 |
| WO | WO-2006/127926 | 4/2001 |
| WO | 01/52904 | 7/2001 |
| WO | WO-01/52875 | 7/2001 |
| WO | WO-01/53268 | 7/2001 |
| WO | 01/55114 | 8/2001 |
| WO | 01/62251 | 8/2001 |
| WO | 01/62252 | 8/2001 |
| WO | WO 01/74296 | 10/2001 |
| WO | 02/18383 | 3/2002 |
| WO | 02/22598 | 3/2002 |
| WO | WO 02/18383 | 3/2002 |
| WO | WO 02/22598 | 3/2002 |
| WO | 02/32861 | 4/2002 |
| WO | WO 02/26716 | 4/2002 |
| WO | WO 02/058697 | 8/2002 |
| WO | 03/004488 | 1/2003 |
| WO | WO 03/033472 | 4/2003 |
| WO | WO 03/087095 | 10/2003 |
| WO | WO 2004/018419 | 3/2004 |
| WO | WO 2004/030620 | 4/2004 |
| WO | WO 2004/031401 | 4/2004 |
| WO | WO 2004/043389 | 5/2004 |
| WO | WO 2004/063151 | 7/2004 |
| WO | WO-2004/063170 | 7/2004 |
| WO | WO-2004/073631 | 9/2004 |
| WO | WO 2004/087153 | 10/2004 |
| WO | WO-2004-103274 | 12/2004 |
| WO | WO-2005/009967 | 2/2005 |
| WO | WO-2005/037306 | 4/2005 |
| WO | WO 2005/046589 | 5/2005 |
| WO | WO-2005/046590 | 5/2005 |
| WO | WO-2005/047244 | 5/2005 |
| WO | WO 2005/053692 | 6/2005 |
| WO | WO 2005/082340 | 9/2005 |
| WO | WO-2006/081445 | 8/2006 |
| WO | WO-2006/127926 | 11/2006 |

OTHER PUBLICATIONS

U.S. Appl. No. 10/839,793, filed May 2004, Barsanti, et al.*
U.S. Appl. No. 10/982,543, filed Nov. 2004, Cai, et al.*
U.S. Appl. No. 10/644,055, filed Aug. 2003, Barsanti, et al.*
Berge et al. J. Pharm. Sci., 1977, vol. 66, No. 1, pp. 1-19.*
"Guideline for the Format and Content of the Human Pharmacokinetic and Bioavailability Section of an Application", Center for Drugs and Biologics, FDA, Department of Health and Human Services, Feb. 1997, pp. 1-18.*
Foekens et al. Cancer Research, 2001, vol. 61, pp. 5407-5414.*
Cecil Textbook of Medicine. 21st Edition, vol. 1, 2000, eds. Goldman and Bennett, pp. 1060-1074.*
Glade-Bender et al. Expert Opin. Biol. Ther., Apr. 2003, vol. 3, No. 2, pp. 263-276.*
Zetter, B. R., "Angiogenesis and Tumor Metastasis," Annu. Rev. Med., 1998, vol. 49, pp. 407-424; published by Annual Review Inc.
MSNBC News Services, "Mixed results on new cancer drug," Nov. 9, 2000.
Gura, T., "Systems for Identifying New Drigs Are Often Faulty," *Science*, vol. 278, pp. 1041-1042.
Dermer, G. B., "Another Anniversary for the War on Cancer," *Biotechnology*, 1994, vol. 12, p. 320.
Freshney, R. I., *Culture of Animal Cells—A Manual of Basic Technique*, 1983, pp. 1-4; published by Alan R. Liss, Inc.
Angiogenesis Foundation, "New Study Shows That Acute Myeloid Leukemia is Angiogenesis-Dependent," Jan. 4, 2000; www.angio.org/newsandviews/ archive2000/jan_4_2000.html.
Hussong, J. W. et al., "Evidence of increased angiogenesis in acute myeloid leukemia," *Blood*, 2000, vol. 95(1), pp. 309-313; The American Society of Hematology.

Kerbel, R.S., "Tumor Angiogenesis: Past, Present and Near Future," *Carcinogenesis*, 2000, vol. 21(3), pp. 505-515; Oxford University Press.

Lundberg, L. G. et al., "Bone Marrow in Polycythemia Vera, Chronic Myelocytic Leukemia, and Myelofibrosis Has an Increased Vascularity," *American Journal of Pathology*, 2000, vol. 157(1), pp. 15-19.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Gruber, G. et al., "Basic Fibroblast Growth Factor is Expressed in CD19/CD11c-Positive Cells in Hairy Cell Leukemia," *Blood*, vol. 94(3), pp. 1077-1085.

Salmon, S. E. et al., *Basic & Clinical Pharmacology, Seventh Edition*, edited by B. Katzung, Appleton & Lange, pp. 29, 881-884 (1998).

Milauer, B. et al., "Glioblastoma Growth Inhibited In Vivo by a Dominant-Negative Flk-1 Mutant," *Nature*, vol. 367, pp. 576-579 (1994); published by Nature Publishing Group.

Pinedo, H. M. et al., "Translational Research: The Role of VEGF in Tumor Angiogenesis," *The Oncologist 2000*, vol. 5 (suppl. 1), pp. 1-5 (2000).

McMahon, G., "VEGF Receptor Signaling in Tumor Angiogenesis," *The Oncologist 2000*, vol. 5 (suppl. 1), pp. 3-10 (2000).

Carmeliet, P. et al. "Angiogenesis in Cancer and Other Diseases," Nature, 407, pp. 249-257 (2000).

Aprelikova, O., et al., "FLT4, a novel Class III Receptor Tyrosine Kinase in chromosome 5q33-qter1," *Cancer Res.*, vol. 52, pp. 746-748, Feb. 1, 1992, published by The American Association for Cancer Research, Stanford University Libraries' High Wire Press, California, United States of America.

Beals, C. R. et al., "Nuclear Export of NF-ATc Enhanced by Glycogen Synthease Kinase-3," *Science*, vol. 275, pp. 1930-1933, Mar. 28, 1997.

Brownlees, J. et al., "Tau phosphorylation in transgenic mice expressing glycogen synthase kinase-3β transgenes," *NeuroReport*, vol. 8, No. 15, pp. 3251-3255, Oct. 20, 1997; published by Rapid Science Publishers.

Chan, T.A. et al., "14-3-σ is required to prevent mitotic catastrophe after DNA damage," *Nature*, vol. 401, pp. 616-620, Oct. 7, 1999; published by Macmillan Magazines Ltd.

Chen, g. et al., "The Mood-Stabilizing Agent Valproate Inhibits the Activity of Glycogen Synthase Kinase-3," *J. Neurochem.*, vol. 72, No. 3, 1999, pp. 1327-1330; published by Lippincott Williams & Wilkins, Inc., Philadelphia.

Chesi, M. et al., "Activated fibroblast growth factor receptor 3 is an oncogene that contributes to tumor progression in multiple myeloma," *Blood*, vol. 97, No. 3, pp. 729-736, Feb. 1, 2001; published by The American Society of Hematology.

Connolly, D., et al., "Human Vascular Permeability Factor," *J. Biol. Chem.*, vol. 264, pp. 20017-20024, 1989, published by The American Society For Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," *J. Clin. Invest.*, vol. 84, pp. 1470-1478, Nov. 1989, published by The American Society for Clinical Investigation, Inc., Stanford University Libraries' High Wire Press, California, United States of America.

Cross, A. E. et al., "The inibition of glycogen synthase kinase-3 by insulin or insulin-like growth factor 1 in the rat skeletal muscle cell line L6 blocked by wortmannin, but not by rapamycin: evidence that wortmannin blocks activation of the mitogen-activated protein kinase pathway in L6 cells between Ras and Raf," *Biochem J.*, vol. 303, pp. 21-26, 1994; (printed in Great Britain).

DeVries, C., et al., "The fms-Like Tyrosine Kinase, a Receptor for Vascular Endothelial Growth Factor," *Science*, vol. 255, pp. 989-991, Feb. 21, 1992, published by The American Society for the Advancement of Science, Stanford University Libraries' High Wire Press, California, United States of America.

Doukas, M. A. et al., "Effect of Lithium on Stem Cell and Stromal Cell Proliferation in vitro," *Exp. Hematol.*, vol. 14, pp. 215-221, 1986; published by International Society for Experimental Hematology.

Ferrara, N., et al., "The Biology of Vascular Endothelial Growth Factor," *Endocrinol. Rev.*, vol. 18, No. 1, pp. 4-25, 1997, published by The Endocrine Society, Stanford University Libraries' High Wire Press, California, United States of America.

Flückiger-Isler, R. E. et al., "Stimulation of rat liver glycogen synthesis by the adenosine kinase inhibitor 5-iodotubercidin," *Biochem. J.*, vol. 292, pp. 85-91, 1993; (printed in Great Britain).

Folkman, J., "Fighting Cancer by Attacking Its Blood Supply," *Scientific American*, vol. 275, pp. 150-154, Sep. 1996, published by Scientific American, Inc., New York, New York, United States of America.

Hammond, W. P. et al., "Lithium Therapy of Canine Cyclic Hematopoiesis," *Blood*, vol. 55, No. 1, pp. 26-28, Jan. 1980.

Heinrich, M. C. et al., "Inhibition of KIT Tyrosine Kinase Activity: A Novel Molecular Approach to the Treatment of KIT-Positive Malignancies," *J. Clin. Oncol.*, vol. 20, No. 6, pp. 1692-1703, Mar. 15, 2002.

Hennequin, L. F., et al., Design and Structure—Activity Relationship of a New Class of Potent VEGF Receptor Tyrosine Kinase Inhibitors,: *J. Med. Chem.*, vol. 42, No. 26, pp. 5369-5389, 1999; published by American Chemical Society, Washington, D.C.

Hirao, A. et al., "DNA Damage-Induced Activation of p53 by the Checkpoint Kinase CHk2," *Science*, vol. 287, pp. 1824-1827, Mar. 10, 2000.

Klein, P. S. et al., "A molecular mechanism for the effect of lithium on development," *Proc. Natl. Acad. Sci. USA*, vol. 93, pp. 8455-8459, Aug. 1996.

Lee, J. et al., "Positive Regulation of Wee1 by Chk1 and 14-3-3 Proteins," *Molecular Biology of the Cell*, vol. 12, pp. 551-563, Mar. 2001; published by The American Society for Cell Biology.

Leung, D., et al., "Vascular Endothelial Growth Factor Is a Secreted Angiogenic Mitogen," *Science*, vol. 246, pp. 1306-1309, Dec. 8, 1989, published by The American Society for the Advancement of Science, Stanford University Libraries' High Wire Press, California, United States of America.

Levis, M. et al., "A FLT3-targeted tyrosine kinase inhibitor is cytotoxic to leukemia cells in vitro and in vivo," *Blood*, vol. 99, No. 11, pp. 3885-3891, Jun. 1, 2002; published by the American Society of Hematology.

Liu, Q. et al., "Chk1 is an essential kinase that is regulated by Atr and required for the $G_2$/M DNA damage checkpoint," *Genes & Development*, vol. 14, 2000, pp. 1448-1459; published by Cold Springs Harbor Laboratory Press.

Lopez-Girona, A. et al., "Nuclear localization of Cdc25 is regulated by DNA damage and a 14-3-3 protein," *Nature*, vol. 397, pp. 172-175, Jan. 14, 1999; published by Macmillan Magazines Ltd.

Lovestone, S. et al., "Alzheimer's disease-like phosphorylation of the microtubule-associated protein tau by glycogen synthase kinase-3 in transfected mammalian cells," *Current Biology*, vol. 44, pp. 1077-1086, Dec. 1, 1994; published by Elsevier Science Ltd.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Maguire, M.P., et al., "A New Series of PDGF Receptor Tyrosine Kinase Inhibitors: 3-Substituted Quinoline Derivatives," *J. Med. Chem.*, vol. 37, No. 14, pp. 2129-2137, 1994; published by American Chemical Society, Washington, D.C.

Massillon, D. et al., "Identification of glycogenic compound 5-iodotubercidin as a general protein kinase inhibitor," *Biochem. J.*, vol. 299, pp. 123-128, 1994; printed in Great Britain.

Matei, S., et al., "Condensation of ethyl 2-benzimidazoleacetate with carbonyl compounds," *Rev. Chim.*, vol. 33, No. 6, pp. 527-530, 1989, published by the Central Institute of Chemistry, Bucharest, Romania.

Mustonen, T., et al., "Endothelial Receptor Tyrosine Kinases Involved in Angiogenesis," *J. Cell Biology*, vol. 129, No. 4, pp. 895-898, May 1995, published by The Rockfeller University Press, New York, New York, United States of America.

Nonaka, S. et al., "Chronic lithium treatment robustly protects neurons in the central nervous system against excitotoxicity by inhibiting N-methyl-D-aspartate receptor-mediated calcium influx," *Proc. Natl. Acad. Sci. USA*, vol. 95, pp. 2642-2647, Mar. 1998.

Parker, L. L. et al., "Inactivation of the p34cdc2-Cyclin B Complex by the Human WEE1 Tyrosine Kinase," *Science*, vol. 257, pp. 1955-1957, Sep. 25, 1992.

Pei, J.-J. et al., "Distribution, Levels, and Activity of Glycogen Synthase Kinase-3 in the Alzheimer Disease Brain," *Journal of Neuropathology and Experimental Neurology*, vol. 56, No. 1, pp. 70-78, Jan. 1997; published by the American Association of Neuropathologists.

Peng, C.-Y. et al., "Mitotic and $G_2$ Checkpoint Control: Regulation of 14-3-3 Protein Binding by Phosphorylation of Cdc25C on Serine-216," *Science*, vol. 277, pp. 1501-1505, Sep. 5, 1997.

Plouet, J., et al., "Isolation and characterization of a newly identified endothelial cell mitogen produced by AtT-20 cells," *EMBO J.*, vol. 8, No. 12, pp. 3801-3806, published by IRL Press.

Quinn, T., et al., "Fetal liver kinase 1 is a receptor for vascular endothelial growth factor and is selectvely expressed in vascular endothelium," *Proc. Natl. Acad. Sci. USA*, vol. 90, pp. 7533-7537, Aug. 1993.

Saito, Y. et al., "The mechanism by which epidermal growth factor inhibits glycogen synthase kinase 3 in A431 cells," *Biochem. J.*, vol. 303, pp. 27-31, 1994; printed in Great Britain.

Sanchez, Y. et al., "Conservation of the Chk1 Checkpoint Pathway in Mammals: Linkage of DNA Damage to Cdk Regulation Through Cdc25," *Science*, vol. 277, pp. 1497-1501, Sep. 5, 1997.

Shibuya, M., et al., "Nucleotide sequence and expression of a novel human receptor-type tyrosine kinase gene (flt) closely related to the fms family," *Oncogene*, vol. 5, pp. 519-524, 1990, published by Macmillan Press Ltd., Stockton Press Company, Great Britain.

Smolich, B.D. et al., "The antiangiogenic protein kinase inhibitors SU5416 and SU6668 inhibit the SCF receptor (c-kit) in a human myeloid leukemia cell line and in acute myeloid leukemia blasts," *Blood*, vol. 97, No. 5, pp. 1413-1421, Mar. 1, 2001; published by The American Society of Hematology.

Stambolic, V. et al., "Lithium inhibits glycogen synthase kinase-3 activity and mimics Wingless signaling in intact cells," *Current Biology*, vol. 6, No. 12, pp. 1664-1668, 1996; published by Current Biology Ltd. ISSN 0960-9822.

Stover, D. R., "Recent advances in protein kinase inhibition: Current molecular scaffolds used for inhibitor synthesis," *Current Opinion in Drug Discovery & Development*, vol. 2, No. 4, pp. 274-285, 1999; published by PharmaPress Ltd., London, United Kingdom.

Sun, T-Q. et al.. "PAR-1 is a Dishevelled-associated kinase and a positive regulator of Wnt signalling," *Nature Cell Biology*, vol. 3, pp. 628-636, Jul. 2001; published by Macmillan Magazines Ltd.

Takashima, A. et al., "tau protein kinase I is essential for amyloid β-protein-induced neurotoxicity," *Proc. Natl. Acad. Sci. USA*, vol. 90, pp. 7789-7793, Aug. 1993.

Takashima, A. et al., "Presenilin 1 associates with glycogen synthase kinase-3β and its substrate tau" *Proc. Natl. Acad. Sci. USA*, vol. 95, pp. 9637-9641, Aug. 1998; published by The National Academy of Sciences.

Terman, B., et al., "Identification of a new endothelial cell growth factor receptor tyrosine kinase," *Oncogene*, vol. 6, pp. 1677-1683, 1991, published by Macmillan Press Ltd., Stockton Press Company, Great Britain.

Thomas, M.D., R. J. et al., "Progress in Geriatrics: Excitatory Amino Acids in Health and Disease," *J. of the American Geriatrics Society*, vol. 43, No. 11, Nov. 1995; published by American Geriatrics Society.

Ukrainets, I., "Effective Synthesis of 3-(Benzimidazol-2-yl)-4-Hydroxy-2-Oxo-1,2-Dihydroquinolines," *Tet. Lett.*, vol. 36, No. 42, pp. 7747-7748, 1995, published by Elsevier Science Ltd., Great Britain.

Ukrainets, I., et al., "2-Carbethoxymethyl-4H-3,1-Benzoxazin-4-One. 3. *Condensation of o-Phenylenediamine," pp. 198-200, translated from *Khimiya Geterotsiklicheskikh Soedinii*, No. 2, pp. 239-241, Feb. 1992, published by Plenum Publ. Corp., London, Great Britain.

Ukrainets, I., et al., "4-Hydroxy-2-Quinolones 7.* Synthesis and Biological Properties of 1-R-3-(2-Benzimidazolyl)-4-Hydroxy-2-Quinolones," pp. 92-94, translated from *Khimiya Geterotsiklicheskikh Soedinii*, No. 1, pp. 105-108, Jan. 1993, published by Plenum Publ. Corp., London, Great Britain.

Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antihyroid Activity of Thio Analogs of 1H-2-OXO-3-(2-Benzimidazolyl)-4-HydroxyQuinoline," *Chem. Heterocyclic Comp.*, vol. 33, No. 5, pp. 600-604, 1997, published by Kluwer Academic Publishers, London, Great Britain.

Ullrich, A., et al., "Signal Transduction by Receptors with Tyrosine Kinase Activity," *Cell*, vol. 61, pp. 203-212, Apr. 20, 1990, published by Cell Press, Cambridge, Massachusetts, United States of America.

van der Geer, P., et al., "Receptor Protein-Tyrosine Kinases and Their Signal Transduction Pathways," *Annu. Rev. Cell Biol.*, vol. 10, pp. 251-337, 1994, published by Annual Reviews, Inc., Palo Alto, California, United States of America.

Vogelstein, B. et al., "Surfing the p53 network," *Nature*, vol. 408, pp. 307-310, Nov. 16, 2000; published by Macmillan Magazines Ltd.

Welsh, G. I. et al., "Glycogen synthase kinase-3 is rapidly inactivated in response to insulin and phosphrylates eukaryotic initiation factor eIF-2B," *Biochem. J.*, vol. 294, pp. 625-629, 1993; printed in Great Britain.

Yamasaki, Y. et al., "Pioglitazone (AD-4833) Ameliorates Insulin Resistance in Patients with NIDDM," *Tohoku J. Exp. Med.*, vol. 183, pp. 173-183, 1997.

Zhao, H. et al., "ATR-Mediated Checkpoint Pathways Regulate Phosphorylation and Activation of Human Chk1," *Molecular and Cellular Biology*, vol. 21, No. 13, pp. 4129-4139, Jul. 2001; published by American Society for Microbiology.

Zhang, Z. et al., "Destabilization of β-catenin by mutations in presenilin-1 potentiates neuronal apoptosis," *Nature*, vol. 395, pp. 698-702, Oct. 15, 1998; published by Macmillan Publishers Ltd.

List of compounds purchased from various vendors (3 pages).

CAS printout for 304876-79-7 Registry File, entry date into Registry File Nov. 29, 2000.

CAS printout for 300591-52-0 Registry File, entry date into Registry File Oct. 31, 2000.

European Search Report dated Feb. 28, 2006 for EP 05017665.0.

Ukrainets, et al., "Effective Synthesis of 3-(Benzimidazol-2-yl)-4-Hydroxy-2-Oxo-1,2-Dihydroquinolines," Tetrahedron Letters, vol. 36, No. 42, 1995, pp. 7747-7748.

Carla Heise, et al., "In vivo Preclinical Evaluation of Tyrosine Kinase Inhibitors with Potent Effects on Tumor Angiogenesis, Growth and Metastasis," Abstract and presentation material for a presentation at the American Association for Cancer Research meeting held in Apr. 2002.

Millauer, B. et al., "Glioblastoma growth inhibited in vivo by a dominant-negative Flk-1 mutant,"*Nature*, vol. 367, pp. 576-579 (1994); published by Nature Publishing Group.

Beebe, J. S. et al., "Pharmacological Characterization of CP-547,632, a Novel Vascular Endothelial Growth Factor Receptor-2 Tyrosine Kinase Inhibitor for Cancer Therapy," *Cancer Research*, vol. 63, pp. 7301-7309, Nov. 2003.

Wedge, S. R. et al., "ZD6474 Inhibits Vascular Endothelial Growth Factor Signaling, Angiogenesis, and Tumor Growth following Oral Adminstration," *Cancer Research*, vol. 62, pp. 4656-4655, Aug. 15, 2002.

Gontero, European Urology, 2004, vol. 46, pp. 296-311.

Kirstein, CA 145:201781, abstract only of Recent Patents on Anti-cancer Drug Discover, 2006, vol. 1(2), pp. 153-161.

Bastin et al. Salt selection and Optimisation procedures for pharmaceutical new chemical entities, organic process research & development 2000, 4, 427-35.

Beck, J. R., "A Direct Synthesis of Benzo[b]thiophene-2-carboxylate Esters Involving Nitro Displacement," *J. Org. Chem.*, vol. 37, No. 21, 1972, pp. 3224-3226.

International Search Report for PCT/US06/19349 dated Sep. 11, 2006.
Kreimeyer, A. et al., "Evaluation and Biological Properties of Reactive Ligands for the Mapping of the Glycine Site on the N-Methyl-D-aspartate (NMDA) Receptor," J. Med. Chem., vol. 42, 1999, pp. 4394-4404; published by American Chemical Society.
Winstead, E., "p53 Gene May Help Fight Tumors," NCI Cancer Bulletin, vol. 4, No. 5, pp. 1-2, 2007.
Yao et al., "Cell-specific but p53-independent Regulation of Vascular Endothelial Growth Factor Expression by Interferons in Human Glioblastoma Cells," Journal of Neuro-Oncology, vol. 76, pp. 219-225, 2006.
Yoo, et al., "Synchronous Elevation of Soluble Intercellular Adhesion Molecule-1 (ICAM-1) and Vascular Cell Adhesion Molecule-1 (VCAM-1) Correlates with Gastric Cancer Progression," Yonsei Medical Journal, vol. 39, No. 1, pp. 27-36, 1998.
Zeng et al., "HDAC3 is crucial in shear- and VEGF-induced stem cell differentiation toward endothelial cells," The Journal of Cell Biology, vol. 174, No1. 7, pp. 1059-1069, 2006.
Supplementary European Search Report for European Patent Application No. EP 06 75 2445 dated Apr. 17, 2009.
Timmer et al.; Lithium Intoxication; J. Am. Soc. Nephro.; vol. 10, pp. 666-674, 1999.
U.S. Appl. No. 10/866,950 Notice of Allowance mailed Jun. 12, 2009.
U.S. Appl. No. 11/982,757 Office Action mailed Aug. 21, 2009.
Berwanger, B. et al., "Loss of a FYN-regulated differentiation and growth arrest pathway in advanced stage neuroblastoma," Cancer Cell, vol. 2, Nov. 2002, pp. 377-386; published by Cell Press.
Caira, Mino R., "Crystalline polymorphism of Organic Compounds," Topics in Current Chemistry, vol. 198, Springer Verlag, 1998.
European Partial Search Report for EP 07011978 dated Sep. 19, 2007.
European Supplementary Search Report for EP 03746614.1 dated May 24, 2007.
International Preliminary Examination Report for PCT/US03/810463 dated Jun. 8, 2004.
International Search Report for PCT/US00/13420 dated Aug. 14, 2000.
International Search Report for PCT/US01/42131 dated Mar. 6, 2002.
International Search Report for PCT/US03/10463 dated Jun. 12, 2003.
Johnson et al., "Relationships between drug activity in NCI preclinical in vitro and in vivo models and early clinical trials," British Journal of Cancer, vol. 84, No. 10, 2001, pp. 1424-1431.
Lee, S. H. et al., "In vivo Target Modulation and Biological Activity of CHIR-258, a Multitargeted Growth Factor Receptor Kinase Inhibitor, in Colon Cancer Models," Clin. Cancer Res., May 15, 2005, vol. 11, No. 10; pp. 3633-3641.
Lopes De Menezes, D. E. et al., "CHIR-258: A Potent Inhibitor of FLT3 Kinase in Experimental Tumor Xenograft Models of Human Acute Myelogenous Leukemia," Clin. Cancer Res., Jul. 15, 2005, vol. 11, No. 14, pp. 5281-5291.
Majolini, M. B. et al., "Dysregulation of the Protein Tyrosine Kinase LCK in Lymphoproliferative Disorders and in Other Neoplasias," Leukemia and Lymphoma, vol. 35(3-4), 1999, pp. 245-254; published by OPA (Overseas Publishers Association) N.V.
Mundy, "Preclinical models of bone metastases," Semin. Oncol., 28(4 Suppl. 11), 2001, pp. 2-8.
Siemeister, G. et al., "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway," Cancer Research, vol. 59, Jul. 1, 1999, pp. 3185-3191.
Suggitt et al., "50 Years of Preclinical Anticancer Drug Screening: Empirical to Target-Driven Approaches," Clinical Cancer Research, vol. 11, 2005, pp. 971-981.

Susa, M. et al., "Src inhibitors: drugs for the treatment of osteoporosis, cancer or both?," TiPS, vol. 21, Dec. 2000, pp. 489-495; published by Elsevier Science Ltd.
Taiwanese Search Report in Application No. 92131830 received Jul. 24, 2009 (English translation only).
Trudel, S. et al., "CHIR-258, a novel, multitargeted tyrosine kinase inhibitor for the potential treatment of t(4;14) multiple myeloma," Blood, Apr. 1, 2005, vol. 105 No. 7, pp. 2941-2948.
Valtola, R. et al., "VEGFR-3 and Its Ligand VEGF-C Are Associated with Angiogenesis in Breast Cancer," American Journal of Pathology, vol. 154, No. 5, May 1999, pp. 1381-1390; published by American Society for Investigative Pathology.
Andre, T., et al., "CPT-11 (Irinotecan) Addition to Bimonthly, High-dose Leucovorin and Bolus and Continuous-infusion 5-Fluorouracil (FOLFIRI) for Pretreated Metastic Colorectal Cancer," European Journal of Cancer, vol. 35, No. 9, 1999, pp. 1343-1347. Compound summary also attached.
Jackman, A.L., et al., "Combination of Raltitrexed with other Cytotoxic Agents: Rationale and Preclinical Observations," European Journal of Cancer, vol. 35, Suppl. 1, Mar. 1999, pp. S3-S8. Compound summary also attached.
Magne, N., et al., "Sequence-dependent effects of ZD 1839 (Iressa) in combination with cytotoxic treatment in human head and neck cancer," British Journal of Cancer, 2002, pp. 819-827.
Morin, Michael J., "From oncogene to drug: development of small molecule tyrosine kinase inhibitors as anti-tumor and anti-angiogenic agents," Oncogene, 2000, pp. 6574-6583.
Noble, et al., "Protein Kinase Inhibitors: Insights into Drug Design from Structure," Science, vol. 303, Mar. 19, 2004, pp. 1800-1805.
Written Opinion received in Singapore App. No. SG 200703449-9 dated Nov. 26, 2009.
Bulusu V. R., "Irinotecan and 5-Flourouracil in Colorectal Cancer: Time for a Pause?," European Journal of Cancer, vol. 34, No. 3, 1998, pp. 286-289.
European Search Report received for EP Appln. No. 03783281.3 mailed Jan. 15, 2010.
European Search Report received for EP Appln. No. 04816941.1 mailed Jan. 14, 2010.
Supplementary Search Report received in Malaysian Appln. No. PI20034345 completed Jan. 14, 2010.
Chekhun (Tschechun), et al., "Current View on the Mechanisms of Drug Resistance of Tumors," Onkologijya, 2000, T.2, No. 1-2, pp. 11-15.
International Search Report for PCT/US2005/005316 dated Nov. 28, 2005.
Trudel, S. et al., "CHIR-258, a novel, multitargeted tyrosine kinase inhibitor for the potential treatment of t(4;14) multiple myeloma," Blood, Apr. 2005, vol. 105, No. 7, pp. 2941-2948.
Lee, S. H. et al., "In vivo Target Modulation and Biological Activity of CHIR-258, a Multitargeted Growth Factor Receptor Kinase Inhibitor, in Colon Cancer Models," Clin. Cancer Res., May 15, 2005, vol. 11, No. 10; pp. 3633-3641.
Lopes de Menezes, D. E. et al., "CHIR-258: A Potent Inhibitor of FLT3 Kinase in Experimental Tumor Xenograft Models of Human Acute Myelogenous Leukemia," Clin. Cancer Res., Jul. 15, 2005, vol. 11, No. 14, pp. 5281-5291.
Grand, et al., Targeting FGFR3 in Multiple Myeloma: Inhibition of t(4;14) Positive Cells by SU5402 and PD173074, Leukemia, 2004, vol. 18, pp. 962-966.
Dalton, et al., "Multiple Myeloma," Hematology, Am. Soc. Hematol. Educ. Program, 2001, 157-77.
International Search Report for PCT/US04/36956 dated Oct. 2, 2006.
Notice of Allowance received for U.S. Appl. No. 11/061,386 dated Jul. 19, 2010.
Notice of Allowance received for U.S. Appl. No. 10/983,174 dated Jul. 8, 2010.
Supplementary European Search Report received for European Appln. No. 04810468.1 dated May 25, 2010 and mailed Jun. 1, 2010.

* cited by examiner

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 1

His His His His His His
  1               5

<210> SEQ ID NO 2
<211> LENGTH: 15
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 2

Gly Gly Leu Phe Asp Asp Pro Ser Tyr Val Asn Val Gln Asn Leu
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 3

Gly Gly Gly Gly Lys Val Glu Lys Ile Gly Glu Gly Thr Tyr Gly Val
1               5                   10                  15

Val Tyr Lys
```

METHODS OF TREATING CANCER AND RELATED METHODS

CROSS-REFERENCES TO RELATED APPLICATIONS

This application claims priority to U.S. Provisional Application No. 60/460,369 filed Apr. 3, 2003; U.S. Provisional Application No. 60/460,493 filed Apr. 3, 2003; U.S. Provisional Application No. 60/460,328 filed Apr. 3, 2003; U.S. Provisional Application No. 60/426,204 filed Nov. 13, 2002; U.S. Provisional Application No. 60/426,282 filed Nov. 13, 2002; U.S. Provisional Application No. 60/426,107 filed Nov. 13, 2002, and U.S. Provisional Application No. 60/517,915 filed on Nov. 7, 2003, each of which is hereby incorporated by reference in its entirety and for all purposes as if fully set forth herein.

FIELD OF THE INVENTION

This invention relates to methods of treating cancer with a receptor tyrosine kinase inhibitor. The invention also relates to methods of measuring the amounts and concentrations of the inhibitor and its metabolites after administration of the inhibitor to a subject.

BACKGROUND OF THE INVENTION

Capillaries reach into almost all tissues of the human body and supply tissues with oxygen and nutrients as well as removing waste products. Under typical conditions, the endothelial cells lining the capillaries do not divide, and capillaries, therefore, do not normally increase in number or size in a human adult. Under certain normal conditions, however, such as when a tissue is damaged, or during certain parts of the menstrual cycle, the capillaries begin to proliferate rapidly. This process of forming new capillaries from pre-existing blood vessels is known as angiogenesis or neovascularization. See Folkman, J. Scientific American 275, 150-154 (1996). Angiogenesis during wound healing is an example of pathophysiological neovascularization during adult life. During wound healing, the additional capillaries provide a supply of oxygen and nutrients, promote granulation tissue, and aid in waste removal. After termination of the healing process, the capillaries normally regress. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients.

Receptor tyrosine kinases (RTKs) are transmembrane polypeptides that regulate developmental cell growth and differentiation, remodeling and regeneration of adult tissues. Mustonen, T. et al., J. Cell Biology 129, 895-898 (1995); van der Geer, P. et al. Ann Rev. Cell Biol. 10, 251-337 (1994). Polypeptide ligands known as growth factors or cytokines, are known to activate RTKs. Signaling RTKs involves ligand binding and a shift in conformation in the external domain of the receptor resulting in its dimerization. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999); Ullrich, A. et al., Cell 61, 203-212 (1990). Binding of the ligand to the RTK results in receptor trans-phosphorylation at specific tyrosine residues and subsequent activation of the catalytic domains for the phosphorylation of cytoplasmic substrates. Id.

Two subfamilies of RTKs are specific to the vascular endothelium. These include the vascular endothelial growth factor (VEGF) subfamily and the Tie receptor subfamily. Class III RTKs include VEGFR-1, VEGFR-2, and VEGFR-3. Shibuya, M. et al., Oncogene 5, 519-525 (1990); Terman, B. et al., Oncogene 6, 1677-1683 (1991); Aprelikova, O. et al., Cancer Res. 52, 746-748 (1992).

Members of the VEGF subfamily have been described as being able to induce vascular permeability and endothelial cell proliferation and further identified as a major inducer of angiogenesis and vasculogenesis. Ferrara, N. et al., Endocrinol. Rev. 18, 4-25 (1997). VEGF is known to specifically bind to RTKs including VEGFR-1 and VEGFR-2. DeVries, C. et al., Science 255, 989-991 (1992); Quinn, T. et al., Proc. Natl. Acad. Sci. 90, 7533-7537 (1993). VEGF stimulates the migration and proliferation of endothelial cells and induces angiogenesis both in vitro and in vivo. Connolly, D. et al., J. Biol. Chem. 264, 20017-20024 (1989); Connolly, D. et al., J. Clin. Invest. 84, 1470-1478 (1989); Ferrara, N. et al., Endocrino. Rew. 18, 4-25 (1997); Leung, D. et al., Science 246, 1306-1309 (1989); Plouet, J. et al., EMBO J 8, 3801-3806 (1989).

Because angiogenesis is known to be critical to the growth of cancer and to be controlled by VEGF and VEGF-RTK, substantial efforts have been undertaken to develop therapeutics that are antagonists of VEGF-RTK to thereby inhibit or retard angiogenesis, and, hopefully, interfere or stop tumor proliferation.

Platelet derived growth factor receptor kinase (PDGFRK) is another type of RTK. PDGF expression has been shown in a number of different solid tumors, from glioblastomas to prostate carcinomas. In these various tumor types, the biological role of PDGF signaling can vary from autocrine stimulation of cancer cell growth to more subtle paracrine interactions involving adjacent stroma and angiogenesis. Therefore, inhibiting the PDGFR kinase activity with small molecules may interfere with tumor growth and angiogenesis.

4-Amino-5-fluoro-3-[6-(4-methylpiperazin-1-yl)-1H-benzimidazol-2-yl]quinolin-2(1H)-one is a small molecule inhibitor of VEGF-RTK, PDGF-RTK and other receptor tyrosine kinases such as fibroblast growth factor receptor (FGF-RTK). This compound has been described in a patent and several patent applications, the entire disclosures of which are incorporated herein by reference and for all purposes: U.S. Pat. No. 6,605,617, U.S. Ser. No. 10/644,055, U.S. Provisional Application Nos. 60/405,729, 60/428,210, and 60/484,048. Specific methods for administering this compound are needed as are methods for determining the metabolic profile of this potent anticancer agent.

SUMMARY OF THE INVENTION

The instant invention provides methods of treating cancer, including leukemias and solid tumors. In particular there are provided methods for attaining sufficient blood levels of 4-amino-5-fluoro-3-[6-(4-methylpiperazin-1-yl)-1H-benzimidazol-2-yl]quinolin-2(1H)-one in a subject to inhibit the growth of a cancer. This compound is an inhibitor of receptor tyrosine kinases. There are further provided compounds as biomarkers and methods for the use of such compounds to monitor the distribution and metabolism of the inhibitor in a subject. In addition, the present invention provides pharmaceutical compositions and medicaments comprising the inhibitor and their methods of use.

Thus, in accordance with the invention, there are provided methods for treating cancer comprising administering to a subject having cancer a sufficient amount of a compound of formula I:

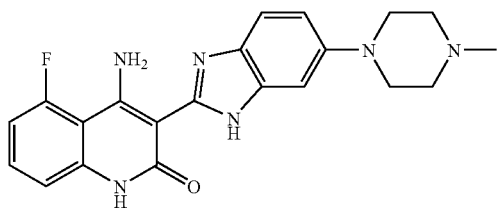

a pharmaceutically acceptable salt thereof, a tautomer thereof, or a pharmaceutically acceptable salt of the tautomer to provide a $C_{max}$ of about 20 to 4000 ng/mL of the compound in the subject's plasma or a $C_{max}$ of about 40 to 8000 ng/mL of the compound in the subject's blood. In some embodiments, the amount of the compound administered is sufficient to provide a $C_{max}$ of about 35 to 2000 ng/mL of the compound in the subject's plasma or a $C_{max}$ of about 70 to 4000 ng/mL of the compound in the subject's blood, a $C_{max}$ of about 50 to 500 ng/mL of the compound in the subject's plasma or a $C_{max}$ of about 100 to 1000 ng/mL of the compound in the subject's blood, a $C_{max}$ of about 50 to 250 ng/mL of the compound in the subject's plasma or a $C_{max}$ of about 100 to 500 ng/mL of the compound in the subject's blood, a $C_{max}$ of about 75 to 150 ng/mL of the compound in the subject's plasma or a $C_{max}$ of about 150 to 300 ng/mL of the compound in the subject's blood, a $C_{max}$ of about 100 to 2000 ng/mL of the compound in the subject's plasma or a $C_{max}$ of about 200 to 4000 ng/mL of the compound in the subject's blood, or a $C_{max}$ of 100 to 1000 ng/mL of the compound in the subject's plasma or a $C_{max}$ of about 200 to 2000 ng/mL of the compound in the subject's blood. The lactate salt of the compound of formula I is administered to the subject in some embodiments, and in some such embodiments the subject is a human. The compound, tautomers, or salts thereof may be formulated as pills, capsules, tablets, gelcaps, caplets, suspensions, aqueous solutions, or other forms as described herein. In some such embodiments, the lactate salt is in an aqueous solution and is administered orally to the human subject. In other embodiments, the compound may be administered by injection.

In a further aspect, the present invention provides methods for treating cancer comprising administering to a subject having cancer a sufficient amount of a compound having formula I, a pharmaceutically acceptable salt thereof, a tautomer thereof, or a pharmaceutically acceptable salt of the tautomer to provide about 10 to 2,000 ng/mL of the compound in the subject's plasma 24 hours after administration or about 20 to 4,000 ng/mL of the compound in the subject's blood 24 hours after administration. In some embodiments, the amount of the compound administered is sufficient to provide about 20 to 1,000 ng/mL of the compound in the subject's plasma 24 hours after administration or about 40 to 2,000 ng/mL of the compound in the subject's blood 24 hours after administration, about 40 to 500 ng/mL of the compound in the subject's plasma 24 hours after administration or about 80 to 1,000 ng/mL of the compound in the subject's blood 24 hours after administration, or about 40 to 250 ng/mL of the compound in the subject's plasma 24 hours after administration or about 80 to 500 ng/mL of the compound in the subject's blood 24 hours after administration. In some embodiments, the subject is a human. Commonly, in the present methods of treating cancer, the lactate salt of the compound of formula I is administered to the subject. In some such embodiments, the lactate salt is in a pill, capsule, tablet, gelcap, caplet, suspension, or aqueous solution and is administered orally to the human subject.

Thus, in certain embodiments of the present methods of treating cancer, the compound of formula I is administered as a pharmaceutical composition or medicament comprising fructose. In some such embodiments, the pharmaceutical composition further comprises a flavoring agent such as TETRAROME mandarine flavor (deterpenated mandarine essential oil). In other embodiments, the pharmaceutical composition further comprises water. Hence, the present methods of treating cancer may further comprise mixing the solid compound of formula I with water to form an aqueous mixture before administering the compound to the subject. The invention further provides the use of the compound of formula I in preparing a medicament for use in treating cancer.

In other embodiments of the methods of treating cancer described herein, the compound is administered as a pharmaceutical composition selected from granules, powders, suspensions, tablets, pills, capsules, gelcaps, caplets, emulsions, syrups, elixirs, slurries, sprays, aerosols, suppositories, or solutions. Preferably, the pharmaceutical composition is selected from tablets, pills, capsules, gelcaps, or caplets.

In still other embodiments of the methods of treating cancer described herein, the compound is administered by injection as a short bolus, slow infusion, or long-term infusion. The injection may be administered once, twice, three times, or four times daily.

In some embodiments of the present methods of treating cancer, the amount of the compound of formula I administered to the subject ranges from 0.25 to 30 mg/kg body weight of the subject. In other embodiments, the amount of the compound administered to the subject ranges from about 25 to 1500 mg/day and, preferably, from about 200 to 500 mg/day.

The present methods of treating cancer are effective against a wide variety of cancers including those in which the cancer to be treated is a solid tumor or leukemia. In particular, the present methods may used to treat cancers such as prostate, colorectal, breast, multiple myeloma, pancreatic, small cell carcinoma, acute myelogenous leukemia, chronic myelogenous leukemia, myelo-proliferative disease, nonsmall cell lung, small cell lung, chronic lymphoid leukemia, sarcoma, melanoma, lymphoma, thyroid, neuroendocrine, renal cell, gastric, gastrointestinal stromal, glioma, brain or bladder.

In some embodiments, the methods of treating cancer described herein further comprise administering the compound of formula I as part of a treatment cycle. Thus, the treatment cycle may comprise administering the amount of the compound of formula I daily for 7, 14, 21, or 28 days, followed by 7 or 14 days without administration of the compound. In some embodiments, the treatment cycle comprises administering the amount of the compound daily for 7 days, followed by 7 days without administration of the compound. A treatment cycle may be repeated one or more times to provide a course of treatment. In addition, the compound may be administered once, twice, three times, or four times daily during the administration phase of the treatment cycle. In other embodiments, the methods further comprise administering the amount of the compound once, twice, three times, or four times daily or every other day during a course of treatment.

There are further provided methods for treating cancer comprising administering to a subject having cancer a sufficient amount of a compound having the formula:

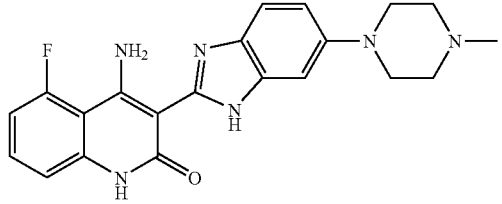

a pharmaceutically acceptable salt thereof, a tautomer thereof, or a pharmaceutically acceptable salt of the tautomer to provide an AUC of about 500 to 60,000 ng*h/mL of the compound in the subject's plasma or about 750 to 120,000 ng*h/mL of the compound in the subject's blood. In other such embodiments, the amount of the compound administered is sufficient to provide an AUC of about 1,000 to 30,000 ng*h/mL of the compound in the subject's plasma or about 1,500 to 60,000 ng*h/mL of the compound in the subject's blood. In other such embodiments, the AUC is about 2,000 to 15,000 ng*h/mL of the compound in the subject's plasma or about 3,000 to 30,000 ng*h/mL of the compound in the subject's blood.

The present invention further provides methods for treating cancer comprising administering to a subject having cancer a compound having formula I, a pharmaceutically acceptable salt thereof, a tautomer thereof, or a pharmaceutically acceptable salt of the tautomer, wherein the amount of compound administered in a first treatment cycle is 25 mg per day, and the amount of compound administered is increased with each subsequent treatment cycle until either 1500 mg of compound is administered to the subject per day or dose-limiting toxicity is observed in the subject. Typically in such methods, the amount of compound administered is doubled with each subsequent treatment cycle after the first. In some embodiments, the treatment cycle comprises administering the same amount of the compound daily for 7 days followed by 7 days without administration of the compound.

In another aspect, the invention provides methods of treating cancer, comprising administering to a subject having cancer, a sufficient amount of a compound having the formula I

I a pharmaceutically acceptable salt thereof, a tautomer thereof, or a pharmaceutically acceptable salt of the tautomer, and exposing the subject to one or both compounds of formula II and formula III selected from:

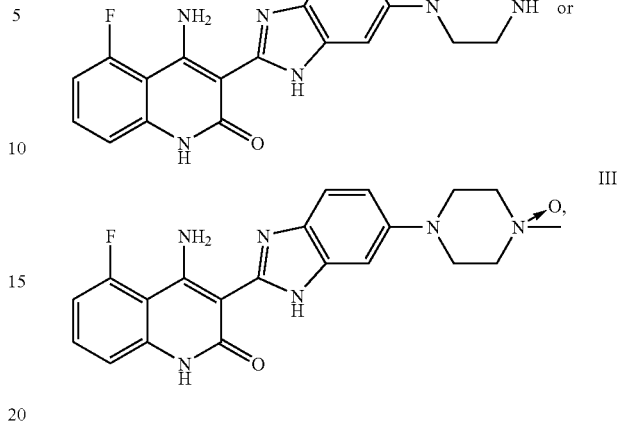

whereby one or both of the compounds of formula II and formula III are produced by metabolism of the compound of formula I by the subject, to provide a combined $C_{max}$ for one or more of the compounds of formula I, formula II, and formula III ranging from about 20 to about 4000 ng/mL in the subject's plasma or a combined $C_{max}$ for one or more of the compounds of formula I, formula II, and formula III ranging from about 40 to about 8000 ng/mL in the subject's blood.

In yet another aspect, the present invention provides methods for treating cancer comprising exposing a subject having cancer to a sufficient amount of one or more compounds having a formula selected from:

an active metabolite thereof, a pharmaceutically acceptable salt thereof, a tautomer thereof, or a pharmaceutically acceptable salt of the tautomer, sufficient to provide a combined $C_{max}$ of about 20 to 4000 ng/mL of the one or more compounds in the subject's plasma or a combined $C_{max}$ of about 40 to 8000 ng/mL of the one or more compound in the subject's blood. In some embodiments, the amount of the one or more compounds provides a $C_{max}$ for one of the compounds of about 35 to 2600 ng/mL in the subject's plasma or a $C_{max}$ for one of the compounds of about 35 to 6000 ng/mL in the subject's blood. In other embodiments, the amount of the one or more compounds provides a $C_{max}$ for one of the compounds of about 35 to 1200 ng/mL in the subject's plasma or a $C_{max}$ for one of the compounds of about 50 to 2400 ng/mL in the subject's blood.

In other aspects of the invention, there are provided methods for determining a metabolic profile for a compound of formula I, a pharmaceutically acceptable salt thereof, a tautomer thereof, or a pharmaceutically acceptable salt of the tautomer, in a subject, the method comprising measuring the amount of at least one metabolite of the compound in one or more samples of urine, blood, or tissue taken from the subject. In some such embodiments, at least one metabolite is an N-oxide compound having formula II:

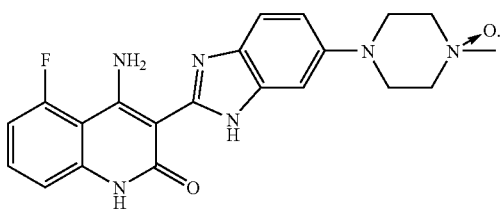

In other such embodiments, at least one metabolite is an N-desmethyl compound having formula III:

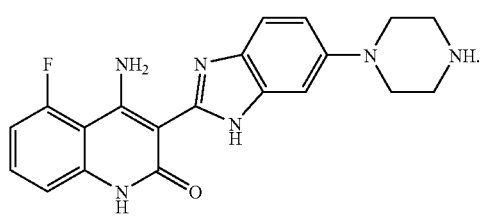

In some such embodiments, the at least one metabolite further includes a second metabolite that is an N-oxide compound of formula II. The amount of metabolites may be measured using techniques, including ultraviolet (UV) spectroscopy and/or liquid chromatography-mass spectroscopy (LC-MS).

In other aspects of the invention, there are provided methods of determining the amount of a compound having formula I, a pharmaceutically acceptable salt thereof, a tautomer thereof, or a pharmaceutically acceptable salt of the tautomer in a subject, the method comprising measuring the amount of the compound in a sample of urine, blood, or tissue taken from the subject after the compound has been administered to the subject. This method may further comprise measuring the amount of a metabolite of the compound in the sample. Metabolites that may be measured include, but are not limited to, the N-oxide compound of formula II and/or the N-desmethyl compound having formula III. In some embodiments, the method further comprises withdrawing two or more samples from the subject at different times after the compound of formula I has been administered to the subject.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

DETAILED DESCRIPTION

Figure 1:
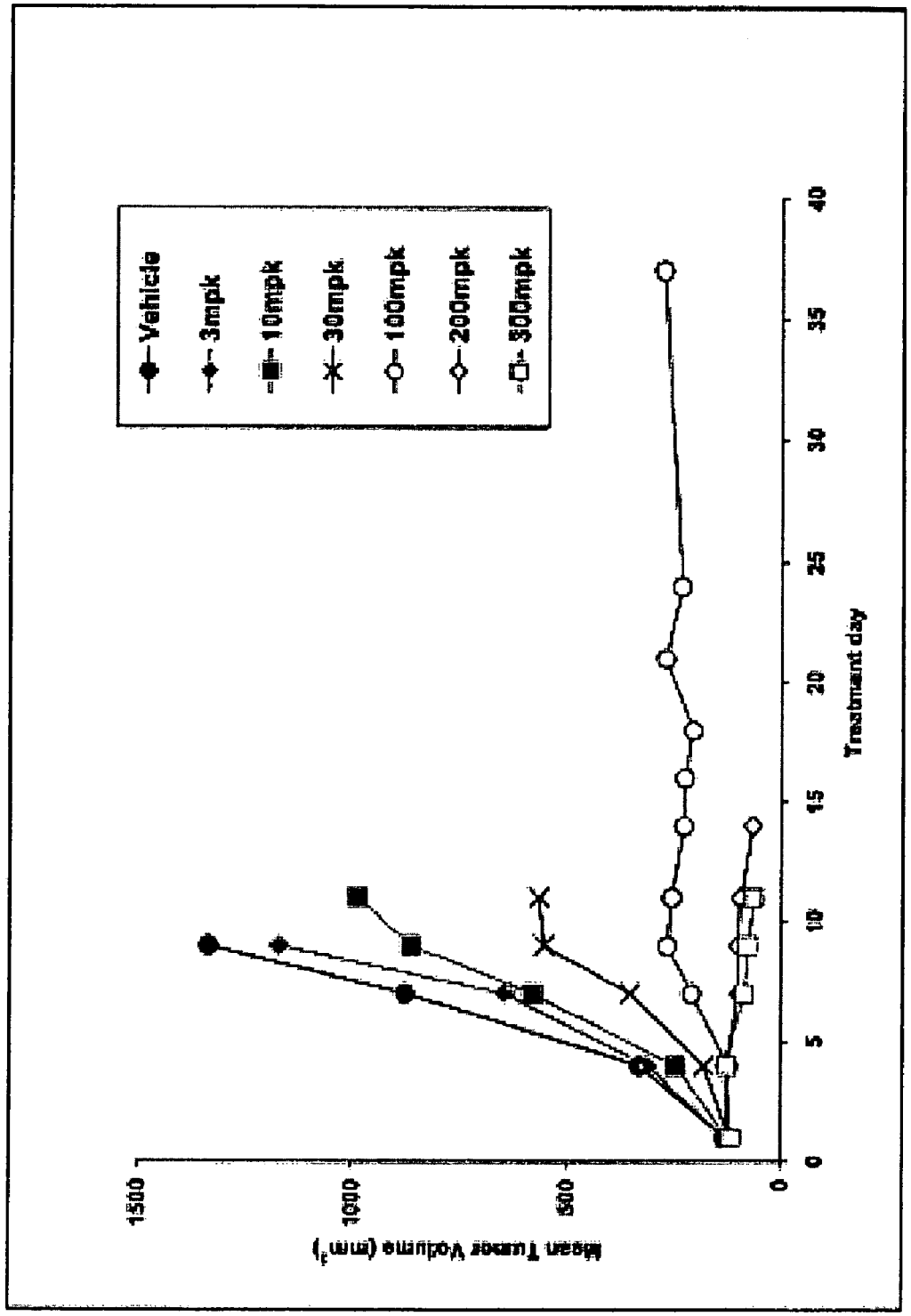
FIG. 1 shows KM12L4a tumor inhibition by the compound of formula I.

The instant invention relates to methods for the treatment of cancer using the compound of formula I, methods for measuring the amount of the compound of formula I and/or its metabolites in biological samples taken from a subject, and pharmaceutical compositions and medicaments comprising the compound of formula I and methods of use thereof.

The following terms and phrases as defined herein are used throughout this specification.

As employed herein, "AUC" refers to area under the curve in a graph of the concentration of a compound in blood plasma over time.

As employed herein, "$C_{max}$" refers to the maximum concentration of a compound in the plasma, tissue, or blood of a subject to which the compound has been administered. $C_{max}$ typically occurs within several hours of administration of a compound to a subject.

Dose limiting toxicity is defined in accordance with the Common Terminology Criteria of Adverse Events Version 3.0 (CTCAE). Thus, dose limiting toxicity occurs upon administration of a compound to a subject if any of the following events are observed within a drug treatment cycle: Grade 4 neutropenia (i.e., absolute neutrophil count (ANC)$\leq$ 500 cells/mm$^3$) for 5 or more consecutive days or febrile neutropenia (i.e., fever$\geq$38.5° C. with an ANC$\leq$1000 cells/mm$^3$); Grade 4 thrombocytopenia (i.e., $\leq$25,000 cells/mm$^3$ or bleeding episode requiring platelet transfusion); Grade 4 fatigue, or a two-point decline in ECOG performance status; Grade 3 or greater nausea, diarrhea, vomiting, and/or myalgia despite the use of adequate/maximal medical intervention; Grade 3 or greater non-hematological toxicity (except fatigue); retreatment delay of more than 2 weeks due to delayed recovery from toxicity related to treatment with compound 1; Grade 2 or greater cardiac toxicity of clinical significance (e.g., a decline in the resting ejection fraction to 40%-$\leq$50% or shortening fraction to 15%-$\leq$24%; cardiac troponin T$\geq$0.05 ng/mL).

Pharmaceutically acceptable salts include a salt with an inorganic base, organic base, inorganic acid, organic acid, or basic or acidic amino acid. As salts of inorganic bases, the invention includes, for example, alkali metals such as sodium or potassium, alkali earth metals such as calcium and magnesium, aluminum, and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, lactic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

It should be understood that the organic compounds according to the invention may exhibit the phenomenon of tautomerism. As the chemical structures within this specification can only represent one of the possible tautomeric forms at a time, it should be understood that the invention encompasses any tautomeric form of the drawn structure. For example, the compound of formula I is shown below with one tautomer, Tautomer Ia:

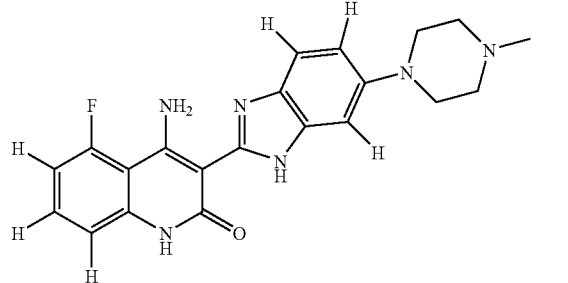

Tautomer Ia

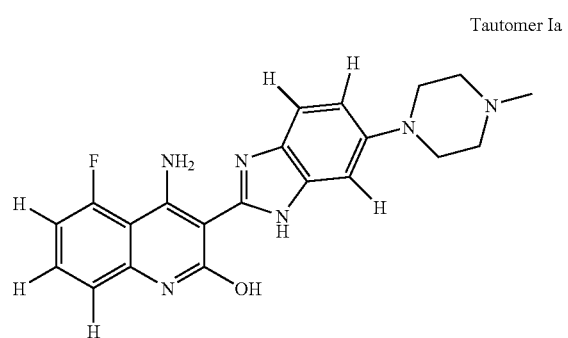

Other tautomers of the compound of formula I, Tautomer Ib and Tautomer Ic, are shown below:

Tautomer Ib

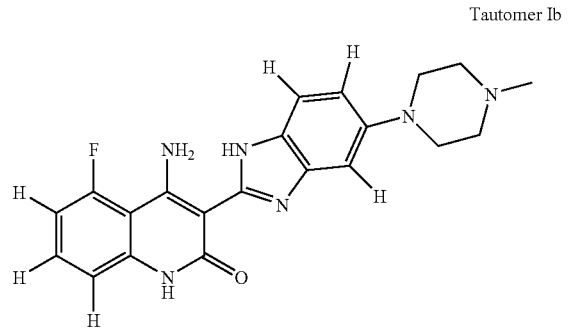

-continued

Tautomer Ic

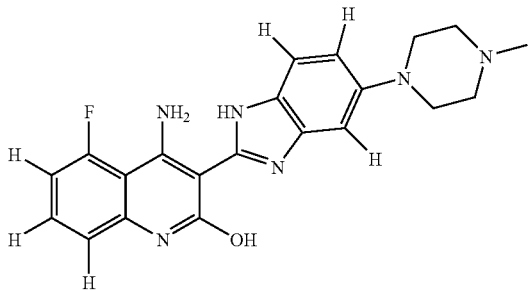

As readily understood by one skilled in the art, a wide variety of functional groups and other structures may exhibit tautomerism, and all tautomers of compounds having formula I are within the scope of the present invention.

The term "subject" as used herein refers to any animal that can experience the beneficial effects of the methods of the invention. Thus, a compound of formula I, pharmaceutically acceptable salts thereof, tautomers thereof, or a pharmaceutically acceptable salt of a tautomer can be administered to any animal that can experience the beneficial effects of the compound in accordance with the methods of treating cancer provided by the invention. Preferably, the animal is a mammal, and in particular a human, although the invention is not intended to be so limited. Examples of other suitable animals include, but are not limited to, rats, mice, monkeys, dogs, cats, cattle, horses, pigs, sheep, and the like.

"Treating" within the context of the instant invention means an alleviation of symptoms associated with a disorder or disease, or halt of further progression or worsening of those symptoms, or prevention or prophylaxis of the disease or disorder. For example, within the context of cancer, successful treatment may include an alleviation of symptoms or halting the progression of the disease, as measured by a reduction in the growth rate of a tumor, a halt in the growth of the tumor, a reduction in the size of a tumor, partial or complete remission of the cancer, or increased survival rate or clinical benefit.

In one aspect, the present invention provides methods for treating cancer including administering to a subject having cancer a sufficient amount of a compound of formula I:

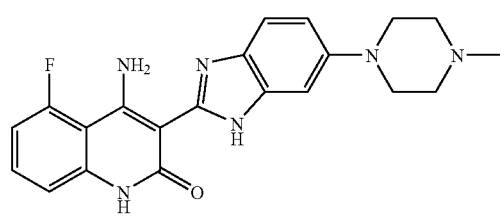

a pharmaceutically acceptable salt thereof, a tautomer thereof, or a pharmaceutically acceptable salt of the tautomer to provide a $C_{max}$ of about 20 to 4000 ng/mL of the compound in the subject's plasma or a $C_{max}$ of about 40 to 8000 ng/mL of the compound in the subject's blood. In some embodiments, the amount of the compound of formula I administered is sufficient to provide a $C_{max}$ of about 35 to 2000 ng/mL of the compound in the subject's plasma or a $C_{max}$ of about 70 to 4000 ng/mL of the compound in the subject's blood, a $C_{max}$ of about 50 to 500 ng/mL of the compound in the subject's plasma or a $C_{max}$ of about 100 to 1000 ng/mL of the compound in the subject's blood, a $C_{max}$ of about 50 to 250 ng/mL of the compound in the subject's plasma or a $C_{max}$ of about 100 to 500 ng/mL of the compound in the subject's blood, a $C_{max}$ of about 75 to 150 ng/mL of the compound in the subject's plasma or a $C_{max}$ of about 150 to 300 ng/mL of the compound in the subject's blood, a $C_{max}$ of about 100 to 2000 ng/mL of the compound in the subject's plasma or a $C_{max}$ of about 200 to 4000 ng/mL of the compound in the subject's blood, or a $C_{max}$ of 100 to 1000 ng/mL of the compound in the subject's plasma or a $C_{max}$ of about 200 to 2000 ng/mL of the compound in the subject's blood. Preferably the amount of the compound administered is sufficient to provide a $C_{max}$ of about 75 to 150 ng/mL of the compound in the subject's plasma or a $C_{max}$ of about 150 to 300 ng/mL of the compound in the subject's blood. Thus, it is to be understood that the $C_{max}$ provided by the sufficient amount of the compound of formula I, tautomers, and salts thereof falls within the given ranges.

In a further aspect, the present invention provides methods for treating cancer comprising administering to a subject having cancer a sufficient amount of a compound having formula I, a pharmaceutically acceptable salt thereof, a tautomer thereof, or a pharmaceutically acceptable salt of the tautomer to provide about 10 to 2,000 ng/mL of the compound in the subject's plasma 24 hours after administration or about 20 to 4,000 ng/mL of the compound in the subject's blood 24 hours after administration. In some embodiments, the amount of the compound administered is sufficient to provide about 20 to 1,000 ng/mL of the compound in the subject's plasma 24 hours after administration or about 40 to 2,000 ng/mL of the compound in the subject's blood 24 hours after administration, about 40 to 500 ng/mL of the compound in the subject's plasma 24 hours after administration or about 80 to 1,000 ng/mL of the compound in the subject's blood 24 hours after administration, or about 40 to 250 ng/mL of the compound in the subject's plasma 24 hours after administration or about 80 to 500 ng/mL of the compound in the subject's blood 24 hours after administration.

Typically, in the methods of treating cancer described herein, the compound of formula I or a tautomer thereof is administered as a pharmaceutically acceptable salt. Salts such as lactate, malate, mesylate, acetate, tartrate, phosphate, sulfate, nitrate, HCl, citrate, or maleate in various molar ratios and in their enantiomeric or racemic forms are suitable. Preferably, the lactate salt of the compound of formula I is administered to a subject such as a human subject. The lactate salt is conveniently administered to the patient in a pill, capsule, tablet, gelcap, caplet, suspension, or aqueous solution and is administered orally. In other embodiments, the compound or salt may be administered by injection as described below.

Thus, in some embodiments of the present methods of treating cancer, the compound of formula I is administered as a pharmaceutical composition or medicament that includes fructose. Such compositions may also include a flavoring agent such as TETRAROME mandarine flavor or the like and/or a diluent, such as water. Hence, the present methods of treating cancer may further include mixing the solid compound of formula I with water to form an aqueous mixture before administering the compound to the subject. The invention further provides the use of the compound I of formula I in preparing a medicament for use in treating cancer.

In some embodiments of the present methods of treating cancer, the amount of the compound of formula I administered to the subject ranges from 0.25 to 30 mg/kg body weight of the subject. In other embodiments, the amount of the compound administered to the subject ranges from about 25 to 1500 mg/subject per day, from about 100 to 1000 mg/subject per day, or from about 200 to 500 mg/subject per day.

The present methods of treating cancer are effective against a wide variety of cancers including those in which the cancer to be treated is a solid tumor or leukemia. In particular, the present methods may used to treat cancers such as prostate, colorectal, breast, multiple myeloma, pancreatic, small cell carcinoma, acute myelogenous leukemia, chronic myelogenous leukemia, myelo-proliferative disease, nonsmall cell lung, small cell lung, chronic lymphoid leukemia, sarcoma, melanoma, lymphoma, thyroid, neuroendocrine, renal cell, gastric, gastrointestinal stromal, glioma, brain or bladder. While not wishing to be bound by theory, it is believed that the present methods of treating cancer are effective against solid tumors because the compound of formula I acts as an angiogenesis inhibitor. More specifically, the compound of formula I and its active metabolites are believed to selectively inhibit certain receptor tyrosine kinases involved in tumor angiogenesis and in leukemias.

In some embodiments, the present methods of treating cancer further include administering the compound of formula I as part of a treatment cycle. A treatment cycle includes an administration phase during which the compound is given to the subject on a regular basis and a holiday, during which the compound is not administered. For example, the treatment cycle may comprise administering the amount of the compound of formula I daily for 7, 14, 21, or 28 days, followed by 7 or 14 days without administration of the compound. In some embodiments, the treatment cycle comprises administering the amount of the compound daily for 7 days, followed by 7 days without administration of the compound. A treatment cycle may be repeated one or more times to provide a course of treatment. In addition, the compound may be administered once, twice, three times, or four times daily during the administration phase of the treatment cycle. In other embodiments, the methods further comprise administering the amount of the compound once, twice, three times, or four times daily or every other day during a course of treatment. A course of treatment refers to a time period during which the subject undergoes treatment for cancer by the present methods. Thus, a course of treatment may extend for one or more treatment cycles or refer to the time period during which the subject receives daily or intermittent doses of the compound of formula I.

There are further provided methods for treating cancer comprising administering to a subject having cancer a sufficient amount of a compound of formula I, a pharmaceutically acceptable salt thereof, a tautomer thereof, or a pharmaceutically acceptable salt of the tautomer to provide an AUC of about 500 to 60,000 ng*h/mL of the compound in the subject's plasma or about 750 to 120,000 ng*h/mL of the compound in the subject's blood. In other such embodiments, the amount of the compound administered is sufficient to provide an AUC of about 1,000 to 30,000 ng*h/mL of the compound in the subject's plasma or about 1,500 to 60,000 ng*h/mL of the compound in the subject's blood. In other such embodiments, the AUC is about 2,000 to 15,000 ng*h/mL of the compound in the subject's plasma or about 3,000 to 30,000 ng*h/mL of the compound in the subject's blood.

In another aspect of the invention, there is provided the use of a compound of formula I, a pharmaceutically acceptable salt thereof, a tautomer thereof, or a pharmaceutically acceptable salt of the tautomer, in the preparation of a medicament, in unit dosage form, for treating cancer, wherein each unit dose of the medicament is sufficient to provide at least one of (a) a $C_{max}$ of about 20 to 4000 ng/mL of the compound in a subject's plasma or a $C_{max}$ of about 40 to 8000 ng/mL of the compound in the subject's blood when it is administered to the subject, (b) about 10 to 2,000 ng/mL of the compound in a subject's plasma 24 hours after administration or about 20 to 4,000 ng/mL of the compound in the subject's blood 24 hours after administration to the subject, or (c) an AUC of about 500 to 60,000 ng*h/mL of the compound in a subject's plasma or about 750 to 120,000 ng*h/mL of the compound in the subject's blood when it is administered to the subject.

In some embodiments of the use of a compound of formula I in the preparation of a medicament for treating cancer, each unit dose is sufficient to provide at least one of (a) a $C_{max}$ of about 50 to 500 ng/mL of the compound in the subject's plasma or a $C_{max}$ of about 100 to 1000 ng/mL of the compound in the subject's blood, (b) about 20 to 1,000 ng/mL of the compound in the subject's plasma 24 hours after administration or about 40 to 2,000 ng/mL of the compound in the subject's blood 24 hours after administration, or (c) an AUC of about 1,000 to 30,000 ng*h/mL of the compound in the subject's plasma or about 1,500 to 60,000 ng*h/mL of the compound in the subject's blood.

In other embodiments, each unit dose is sufficient to provide at least one of (a) a $C_{max}$ of about 50 to 250 ng/mL of the compound in the subject's plasma or a $C_{max}$ of about 100 to 500 ng/mL of the compound in the subject's blood, (b) about 40 to 500 ng/mL of the compound in the subject's plasma 24 hours after administration or about 80 to 1,000 ng/mL of the compound in the subject's blood 24 hours after administration, or (c) an AUC of about 2,000 to 15,000 ng*h/mL of the compound in the subject's plasma or about 3,000 to 30,000 ng*h/mL of the compound in the subject's blood.

In still other embodiments, each unit dose is sufficient to provide at least one of (a) a $C_{max}$ of about 75 to 150 ng/mL of the compound in the subject's plasma or a $C_{max}$ of about 150 to 300 ng/mL of the compound in the subject's blood, or (b) about 40 to 250 ng/mL of the compound in the subject's plasma 24 hours after administration or about 80 to 500 ng/mL of the compound in the subject's blood 24 hours after administration.

In another embodiment, each unit dose is sufficient to provide a $C_{max}$ of about 100 to 2000 ng/mL of the compound in the subject's plasma or a $C_{max}$ of about 200 to 4000 ng/mL of the compound in the subject's blood; or a $C_{max}$ of 100 to 1000 ng/mL of the compound in the subject's plasma or a $C_{max}$ of about 200 to 2000 ng/mL of the compound in the subject's blood.

Typically, in the uses of the compound of formula I described herein, the lactate salt of the compound is used to prepare the medicament. Such medicaments are suitable for oral administration. The unit dosage form of the medicament includes but is not limited to a pill, capsule, tablet, gelcap, caplet, suspension, or aqueous solution. In addition, the medicament is suitable for administration by injection as a short bolus, slow infusion, or long-term infusion.

The compounds of formula I, formula II, and formula III may be accompanied with instructions that describe any of the methods of the invention. Therefore, in some embodiments, the invention provides at least one compound of formula I, formula II, and/or formula III in combination with instructions for use in a method of treating cancer or analyzing the metabolic profile of the compound of formula I.

The present invention further provides methods for treating cancer comprising administering to a subject having cancer a compound having formula I, a pharmaceutically acceptable salt thereof, a tautomer thereof, or a pharmaceutically acceptable salt of the tautomer, wherein the amount of compound administered in a first treatment cycle is 25 mg per day, and the amount of compound administered is increased with each subsequent treatment cycle until either 1500 mg of compound is administered to the subject per day or dose-limiting toxicity is observed in the subject. Typically in such methods, the amount of compound administered is doubled with each subsequent treatment cycle after the first. In some embodiments, the treatment cycle comprises administering the same amount of the compound daily for 7 days followed by 7 days without administration of the compound.

Likewise, in some embodiments of the use of a compound of formula I in the preparation of a medicament as described herein, each unit dose of the medicament includes from 0.25 to 30 mg/kg of the compound, tautomer, and/or salts based on the body weight of the subject. Furthermore, each unit dose of the medicament may include an amount of the compound, tautomer, and/or salts ranging from 25 to 1500 mg. The medicament may be arranged in a kit comprising 7, 14, 21 or 28 daily amounts of said unit doses, the kit being suitable for use in a treatment cycle comprises administering the daily amount of the compound for each of 7, 14, 21, or 28 days, followed by 7 or 14 days without administration of the compound.

In another aspect, the invention provides methods of treating cancer, comprising administering to a subject having cancer, a sufficient amount of a compound having the formula I

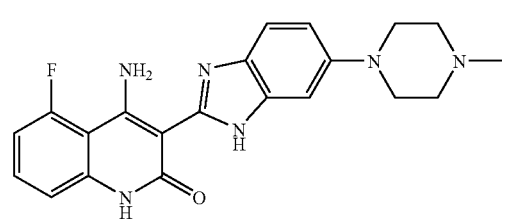

a pharmaceutically acceptable salt thereof, a tautomer thereof, or a pharmaceutically acceptable salt of the tautomer, and exposing the subject to one or both compounds of formula II and formula III selected from:

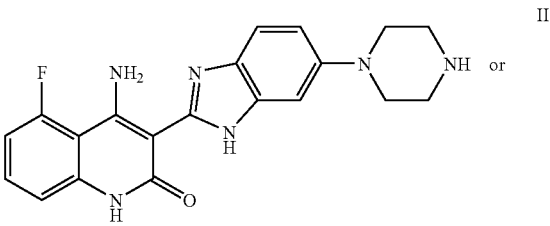

-continued

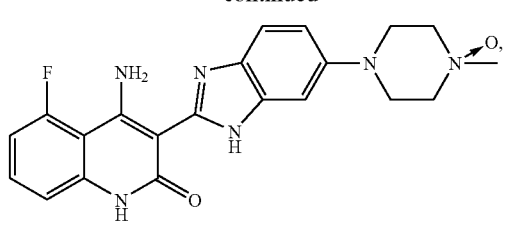

III whereby one or both of the compounds of formula II and formula III are produced by metabolism of the compound of formula I by the subject, to provide a combined $C_{max}$ for one or more of the compounds of formula I, formula II, and formula III ranging from about 20 to about 4000 ng/mL in the subject's plasma or a combined $C_{max}$ for one or more of the compounds of formula I, formula II, and formula III ranging from about 40 to about 8000 ng/mL in the subject's blood.

In yet another aspect, the present invention provides methods for treating cancer comprising exposing a subject having cancer to a sufficient amount of one or more compounds having a formula selected from:

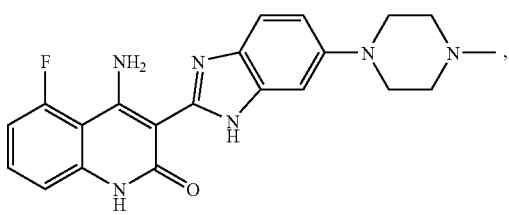

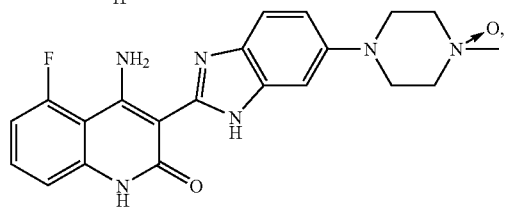

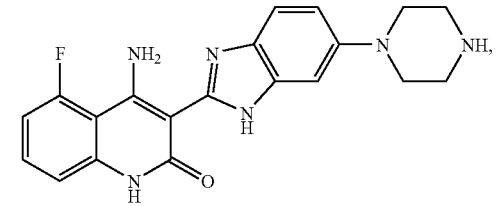

an active metabolite thereof, a pharmaceutically acceptable salt thereof, a tautomer thereof, or a pharmaceutically acceptable salt of the tautomer, sufficient to provide a combined $C_{max}$ of about 20 to 4000 ng/mL of the one or more compounds in the subject's plasma or a combined $C_{max}$ of about 40 to 8000 ng/mL of the one or more compound in the subject's blood. In some embodiments, the amount of the one or more compounds provides a $C_{max}$ for one of the compounds of about 35 to 2600 ng/mL in the subject's plasma or a $C_{max}$ for one of the compounds of about 35 to 6000 ng/mL in the subject's blood. In other embodiments, the amount of the one or more compounds provides a $C_{max}$ for one of the compounds of about 35 to 1200 ng/mL in the subject's plasma or a $C_{max}$ for one of the compounds of about 50 to 2400 ng/mL in the subject's blood. In some embodiments, the compound of formula:

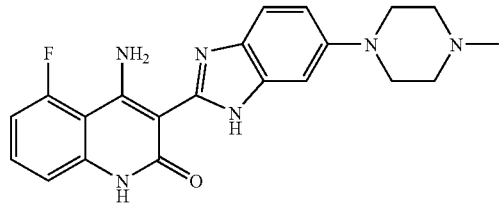

a pharmaceutically acceptable salt thereof, a tautomer thereof, or a pharmaceutically acceptable salt of the tautomer is administered to the subject. In other embodiments, the compound of formula:

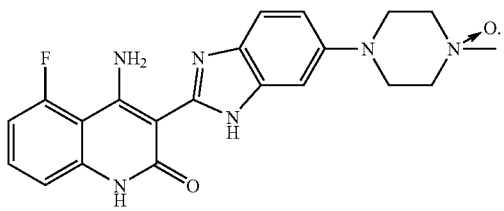

a pharmaceutically acceptable salt thereof, a tautomer thereof, or a pharmaceutically acceptable salt of the tautomer is administered to the subject. In yet other embodiments, the compound of formula:

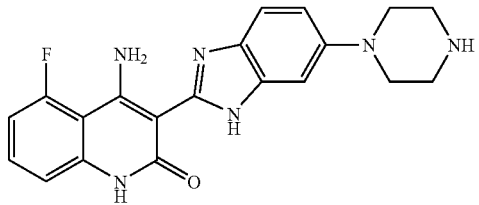

a pharmaceutically acceptable salt thereof, a tautomer thereof, or a pharmaceutically acceptable salt of the tautomer is administered to the subject.

In determining the safety and/or efficacy of a compound of formula I for a particular disease, it is important to be able to monitor the pharmacokinetics and pharmacodynamics of the compound in a subject after administration of the compound. Thus, in accordance with one aspect of the invention, there are provided methods for determining a metabolic profile for a compound of formula I, a pharmaceutically acceptable salt thereof, a tautomer thereof, or a pharmaceutically acceptable salt of the tautomer, in a subject. The method includes measuring the amount of at least one metabolite of the compound in one or more samples of urine, blood, or tissue taken from the subject. Metabolites that may be measured by the method include an N-oxide compound having formula II:

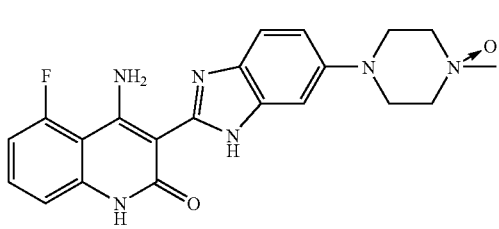

also known as 4-amino-5-fluoro-3-[6-(4-methyl-4-oxidopiperazin-1-yl)-1H-benzimidazol-2-yl]quinolin-2(1H)-one, and the N-desmethyl compound having formula III:

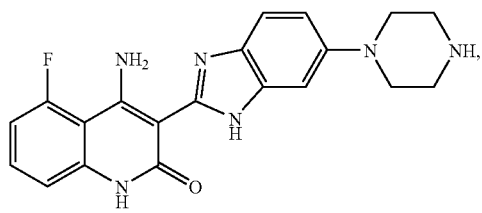

also known as 4-amino-5-fluoro-3-[6-(piperazin-1-yl)-1H-benzimidazol-2-yl]quinolin-2(1H)-one. In some such methods of determining the metabolic profile of a compound of formula I, the methods include measuring the amount of the metabolite of formula II and the metabolite of formula II. The amounts of metabolites may be measured using techniques well known to those skilled in the art, including ultraviolet (UV) spectroscopy or liquid chromatography-mass spectroscopy (LC-MS).

In other aspects of the invention, there are provided methods of determining the amount of a compound having formula I, a pharmaceutically acceptable salt thereof, a tautomer thereof, or a pharmaceutically acceptable salt of the tautomer in a subject. The method includes measuring the amount of the compound in a sample of urine, blood, or tissue taken from the subject after the compound has been administered to the subject. This method may further include measuring the amount of a metabolite of the compound in the sample. Metabolites that may be measured include, but are not limited to, the N-oxide compound of formula II and/or the N-desmethyl compound of formula III. In some embodiments, the method further includes withdrawing two or more samples from the subject at different times after the compound of formula I has been administered to the subject.

In another aspect, there is provided the compound having formula I, a pharmaceutically acceptable salt thereof, a tautomer thereof, or a pharmaceutically acceptable salt of the tautomer, for use in a method of treating cancer comprising administering an amount of said compound to a cancer patient, in an amount sufficient to provide at least one of (a) a $C_{max}$ of about 20 to 4000 ng/mL of the compound in a subject's plasma or a $C_{max}$ of about 40 to 8000 ng/mL of the compound in the subject's blood when it is administered to the subject, (b) about 10 to 2,000 ng/mL of the compound in a subject's plasma 24 hours after administration or about 20 to 4,000 ng/mL of the compound in the subject's blood 24 hours after administration to the subject, or (c) an AUC of about 500 to 60,000 ng*h/mL of the compound in a subject's plasma or about 750 to 120,000 ng*h/mL of the compound in the subject's blood when it is administered to the subject.

In some embodiments of the compound for use in a method of treating cancer, each unit dose is sufficient to provide at least one of (a) a $C_{max}$ of about 50 to 500 ng/mL of the compound in the subject's plasma or a $C_{max}$ of about 100 to 1000 ng/mL of the compound in the subject's blood, (b) about 20 to 1,000 ng/mL of the compound in the subject's plasma 24 hours after administration or about 40 to 2,000 ng/mL of the compound in the subject's blood 24 hours after administration, or (c) an AUC of about 1,000 to 30,000 ng*h/mL of the compound in the subject's plasma or about 1,500 to 60,000 ng*h/mL of the compound in the subject's blood.

In other embodiments of the compound for use in a method of treating cancer, each unit dose is sufficient to provide at least one of (a) a $C_{max}$ of about 50 to 250 ng/mL of the compound in the subject's plasma or a $C_{max}$ of about 100 to 500 ng/mL of the compound in the subject's blood, (b) about 40 to 500 ng/mL of the compound in the subject's plasma 24 hours after administration or about 80 to 1,000 ng/mL of the compound in the subject's blood 24 hours after administration, or (c) an AUC of about 2,000 to 15,000 ng*h/mL of the compound in the subject's plasma or about 3,000 to 30,000 ng*h/mL of the compound in the subject's blood.

In still other embodiments of the compound for use in a method of treating cancer, each unit dose is sufficient to provide at least one of (a) a $C_{max}$ of about 75 to 150 ng/mL of the compound in the subject's plasma or a $C_{max}$ of about 150 to 300 ng/mL of the compound in the subject's blood, or (b) about 40 to 250 ng/mL of the compound in the subject's plasma 24 hours after administration or about 80 to 500 ng/mL of the compound in the subject's blood 24 hours after administration.

In yet other embodiments, each unit dose is sufficient to provide a $C_{max}$ Of about 100 to 2000 ng/mL of the compound in the subject's plasma or a $C_{max}$ of about 200 to 4000 ng/mL of the compound in the subject's blood; or each unit dose is sufficient to provide a $C_{max}$ of 100 to 1000 ng/mL of the compound in the subject's plasma or a $C_{max}$ of about 200 to 2000 ng/mL of the compound in the subject's blood.

There is further provided the use of a metabolite for determining a metabolic profile for a compound having formula I, a pharmaceutically acceptable salt thereof, a tautomer thereof, or a pharmaceutically acceptable salt of the tautomer, in a subject, the metabolite comprising at least one of an N-oxide compound of formula:

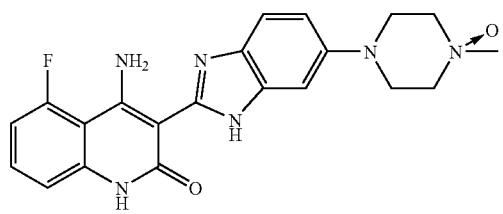

or an N-desmethyl compound of formula:

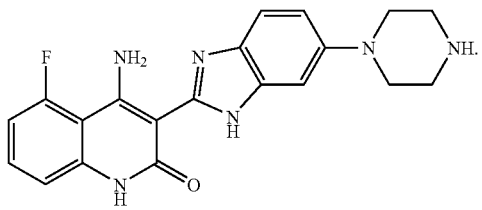

The instant invention also provides for compositions which may be prepared by mixing one or more compounds of the instant invention, or pharmaceutically acceptable salts or tautomers thereof, with pharmaceutically acceptable carriers, excipients, binders, diluents or the like, to treat or ameliorate a variety of disorders. Examples of such disorders include, but are not limited to cancer, including prostate, colorectal, breast, multiple myeloma, pancreatic, small cell carcinoma, acute myelogenous leukemia, chronic myelogenous leukemia, myelo-proliferative disease, nonsmall cell lung, small cell lung, chronic lymphoid leukemia, sarcoma, melanoma, lymphoma, thyroid, neuroendocrine, renal cell, gastric, gastrointestinal stromal, glioma, brain or bladder. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as by injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are fructose, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, a thickeners, buffers, a sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00/33813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

Thus, in the present methods of treating cancer described herein, the compound may be administered by injection as a short bolus, slow infusion, or long-term infusion. The injection may be administered once, twice, three times, or four times daily. A short bolus is generally administered over a period of about 1 to 30 minutes; a slow infusion is generally administered over a period of about 30 minutes to 6 hours; and a long-term infusion is generally administered for a period from over 6 hours up to about seven days.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

A therapeutically effective dose refers to that amount of the compound that results in amelioration of symptoms. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant invention. A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The present invention also provides methods of enhancing anticancer activity in a human or non-human animal. The method comprises administering an effective amount of a compound, or composition, of the instant invention to said mammal or non-human animal. Effective amounts of the compounds of the instant invention include those amounts that inhibit RTK, which are detectable, for example, by an assay herein described, or any other assay known by those skilled in the art that detect signal transduction, in a biochemical pathway, through activation of G-protein coupled receptors, for example, by measuring an elevated cAMP level as compared to a control model. Effective amounts may also include those amounts which alleviate symptoms of a RTK disorder treatable by inhibiting RTK.

An RTK disorder, or RTK-mediated disease, which may be treated by those methods provided, include any biological disorder or disease in which an RTK is implicated, or which inhibition of and RTK potentiates a biochemical pathway that is defective in the disorder or disease state. Examples of such diseases are cancers such as prostate, colorectal, breast, multiple myeloma, pancreatic, small cell carcinoma, acute myelogenous leukemia, chronic myelogenous leukemia, or myelo-proliferative disease.

Synthesis of compound 1 has been disclosed in U.S. Pat. No. 6,605,617. To confirm the identities of compounds 2 and 3, metabolites of compound 1, compounds 2 and 3, were independently synthesized as shown in Example 6.

The present invention, thus generally described, will be understood more readily by reference to the following examples, which are provided by way of illustration and are not intended to be limiting of the present invention.

EXAMPLES

The following abbreviations and terms are used throughout the Examples:
ATP: Adenosine triphosphate
AUC: Area under the curve
BSA: Bovine serum albumin
DMSO: Dimethylsulfoxide
EDTA: Ethylenediamine tetraacetic acid
ERK: Extracellular regulated kinase
Hepes: N-(2-hydroxyethyl) piperazine-N'-(2-ethanesulfonic acid)
HPLC: High perfomance liquid chromatography
HMVEC: Human microvascular endothelial cells
kg: Kilogram
LC: Liquid Chromatography
MAPK: Mitogen activated protein kinase
MS: Mass Spectroscopy
MeOH: Methanol
mg: Milligram
mL: Milliliter
MTS: [3-(4,5-dimethyl-2-yl)-5-(3-carboxymethoxyphenyl)-2-(4-sulfophenyl)-2H-tetrazolium, inner salt
nM: Nanomolar
PBS: Phosphate buffered saline
NMR: Nuclear magnetic resonance spectroscopy
RT-PCR: Reverse transcriptase-polymerase chain reaction
SCF: Stem Cell Factor
TFA: Trifluoroacetic acid
$T_{1/2}$: Half life—the time required for 50% of a compound to be eliminated from a biological system.
μg: Microgram(s)
μL: Microliter(s)
μM: Micromolar
UV: Ultraviolet spectroscopy Example 1

The antiproliferative activities of 4-amino-5-fluoro-3-[6-(4-methylpiperazin-1-yl)-1H-benzimidazol-2-yl]quinolin-2 (1H)-one (compound 1) were tested against a large number of cancer cell lines and primary non-malignant cell lines. Methods were as follows: Cells were plated in 96-well plates; after three to five hours gelling time for adherent cell lines delusions of the compounds were added, three days later viable cells were determined by adding MTS solution (Promega). Absorbance at 490 nm was measured and $EC_{50}$ values calculated using non linear regression. For the HMVEC assay, compounds were incubated with the cells for three days in the presence of five ng/mL recombinant VEGF. For the SCF/c-KIT assay the TF-1 and H526 cells were incubated for three days in the presence of 40 ng/mL and 100 ng/mL recombinant SCF, respectively. Proliferation was assayed by adding MTS solution and measuring the absorbance at 490 nm. $EC_{50}$s were calculated by non-linear regression. Results are shown in Table 1.

In a subset of the cancer cell lines and the endothelial cells, proliferation was inhibited with $EC_{50} \leq 50$ nM, consistent with their dependence on an RTK targeted by compound 1 (MV4; 11: expression of constitutively active FLT3; HMVEC: VEGFR2 mediated proliferation; TF-1: c-KIT mediated proliferation) with the exception of the KM12L4a cell line. Even though this cell line does express some of the targeted RTKs (e.g., VEGFR % and PDGFR determined by RT-PCR), experiments showed that the inhibition of these individual RTKs does not fully explain the potent antiproliferative effects observed with compound 1. This finding suggests that either the inhibition of multiple RTKs or as yet unidentified effects may be responsible for the antiproliferative effect mediated by compound 1 in this cell line.

The majority of cell lines showed an antiproliferative response when incubated with compound 1 with $EC_{50}$s between 1 and 10 μM including two primary cell lines HMEC (human normal mammary epithelial cells) and PrEC (normal human prostate epithelial cells). Consistent with in vitro results, the growth of both the KM12L4a and MV4;11 xenografts in mice were potently inhibited by compound 1 in vivo.

TABLE 1

| $EC_{50} \leq 50$ nM | $EC_{50}$ 0.4-1 μM | $EC_{50}$ 1-10 μM | $EC_{50}$ > 10 μM |
|---|---|---|---|
| MV4; 11 (AML) | RS4 (ALL) | MDA-MB435 (breast cancer) SKOV3 (ovarian cancer) | U87 (brain cancer) |
| KM12L4a (colon cancer) | 4T1 (mouse breast cancer) | | |
| HMVEC (VEGF/VEGF R2 mediated; endothelium) | | K562 (CML) Ku812 (CML) MOLT-4 (ALL) ARH77 (multiple myeloma) | |
| TF-1 (SCF/ c-KIT mediated; AML) | | HCT116 (colon cancer) Du145 (prostate cancer) PC3 (prostate cancer) H209 (lung cancer) H226 (lung cancer) HT29 (colon cancer) SW620 (colon cancer) PrC (normal prostate epithelium) HMEC (normal mammary epithelium) | |

[a] all cell lines tested were of human origin unless otherwise noted.

Example 2

Two metabolites of compound 1 were identified and partially characterized in pooled rat plasma from a 2 week toxicology study. Day 1 and day 14 dosed animal plasmas were analyzed by UV and LC/MS from once a day 30 or 80 mg/kg, PO, dose groups. The two identified metabolites were the piperazine N-oxide compound of formula II (compound 2) and the N-demethylated compound of formula III (compound 3) (see Example 6 for synthesis and characterization of these compounds). Estimated levels of the metabolites (based on UV absorbance and in comparison to known levels of compound 1 quantified in the same samples from previous analyses) are given in Table 2. The N-desmethyl metabolite was found to be in substantially lower abundance than compound 1 in all samples of post dosed pooled plasmas. The N-oxide metabolite was observed to be present in lower abundance than compound 1 except at 24 hours on day 14 in the 80 mg/kg dose group and 1-2 hours on day 1 in the 30 mg/kg dose group (Table 2). The metabolic profile does not change with dose or duration of dose. Generally the metabolite levels increase in tandem with compound 1 levels with dose escalation.

With both dose groups, the duration of dose, Day 1 vs 14, does not appear to result in an increase in plasma levels of metabolites alone (Table 2) or as compared to compound 1 levels. Compound 1 levels decrease with duration of dose and this is reflected by a decrease in metabolite levels as well. This suggests that time dependent reduction in exposure of compound 1 is not reflected in increased metabolism. The day 14, 24 hr samples contained compound 1 and metabolites at lower levels than the 24 hour samples on day 1 indicating that there is no accumulation of metabolites or compound 1 with a once a day dosage regimen of 30 or 80 mg/kg. The N-oxide metabolite is present in higher abundance than the N-desmethyl metabolite at all assayed time points in the 80 mg/kg dose group and in all but the 24 hr time points after day 1 in the 30 mg/kg dose group. The N-desmethyl metabolite levels appear to fall more slowly than that of compound 1 suggesting a longer $T_{1/2}$ and indicating that the plasma levels of this metabolite are likely determined by its rate of elimination and not its rate of formation as is, in contrast, likely for the N-oxide.

TABLE 2

Compound 1 Levels and Estimated Compound 1 Metabolite Levels in Rat Plasma

| Dose (mg/kg) | Day | Sample Time (hr) | Des-CH$_3$ (ng/ml)[1] | N-oxide (ng/ml)[1] | Compound 1 (ng/ml)[2] |
|---|---|---|---|---|---|
| 30 | 1 | 0 | 0 | 0 | 0 |
| 30 | 1 | 1-2 | 14 | 1090 | 635 |
| 30 | 1 | 4-8 | 48 | 310 | 943 |
| 30 | 1 | 24 | 22 | 25 | 54 |
| 30 | 14 | 0 | 6 | 1.3 | 20 |
| 30 | 14 | 1-2 | 6 | 135 | 467 |
| 30 | 14 | 4-8 | 12 | 220 | 442 |
| 30 | 14 | 24 | 4 | 0.4 | 8 |
| 100 | 1 | 0 | 0 | 0 | 0 |
| 100 | 1 | 1-2 | 35 | 424 | 1212 |
| 100 | 1 | 4-8 | 84 | 779 | 2075 |
| 100 | 1 | 24 | 83 | 137 | 500 |
| 100 | 14 | 0 | 15 | 67 | 162 |
| 100 | 14 | 1-2 | 17 | 122 | 628 |
| 100 | 14 | 4-8 | 19 | 533 | 1099 |
| 100 | 14 | 24 | 10 | 102 | 33 |

[1] Metabolite levels estimated based on metabolite UV absorbance areas in comparison to compound 1 UV areas and using previously reported compound 1 levels.
[2] Compound 1 levels previously quantified in a separate study from the same plasma samples analyzed herein.

Example 3

In Vitro Kinase Assays for Receptor Tyrosine Kinases

The kinase activity of a number of protein tyrosine kinases was measured by providing ATP and an appropriate peptide or protein containing a tyrosine amino acid residue for phosphorylation, and assaying for the transfer of phosphate moiety to the tyrosine residue. Recombinant proteins corresponding to the cytoplasmic domains of the FLT-1 (VEGFR1), VEGFR2, VEGFR3, Tie-2, PDGFRα, PDGFRβ, and FGFR1 receptors were expressed in Sf9 insect cells using a Baculovirus expression system (InVitrogen) and may be purified via Glu antibody interaction (for Glu-epitope tagged constructs) or by Metal Ion Chromatography (for $His_6$ (SEQ ID NO: 1) tagged constructs). For each assay, test compounds were serially diluted in DMSO and then mixed with an appropriate kinase reaction buffer plus ATP. Kinase protein and an appropriate biotinylated peptide substrate were added to give a final volume of 50-100 μL, reactions were incubated for 1-3 hours at room temperature and then stopped by addition of 25-50 μL of 45 mM EDTA, 50 mM Hepes pH 7.5. The stopped reaction mixture (75 μL) was transferred to a streptavidin-coated microtiter plate (Boehringer Mannheim) and incubated for 1 hour. Phosphorylated peptide product was measured with the DELFIA time-resolved fluorescence system (Wallac or PE Biosciences), using a Europium labeled anti-phosphotyrosine antibody PT66 with the modification that the DELFIA assay buffer was supplemented with 1 mM $MgCl_2$ for the antibody dilution. Time resolved fluorescence was read on a Wallac 1232 DELFIA fluorometer or a PE Victor II multiple signal reader. The concentration of each compound for 50% inhibition ($IC_{50}$) was calculated employing non-linear regression using XL Fit data analysis software.

FLT-1, VEGFR2, VEGFR3, FGFR3, Tie-2, and FGFR1 kinases were assayed in 50 mM Hepes pH 7.0, 2 mM $MgCl_2$, 10 mM $MnCl_2$, 1 mM NaF, 1 mM DTT, 1 mg/mL BSA, 2 μM ATP, and 0.20-0.50 μM corresponding biotinylated peptide substrate. FLT-1, VEGFR2, VEGFR3, Tie-2, and FGFR1 kinases were added at 0.1 μg/mL, 0.05 μg/mL, or 0.1 μg/mL respectively. For the PDGFR kinase assay, 120 μg/mL enzyme with the same buffer conditions as above was used except for changing ATP and peptide substrate concentrations to 1.4 μM ATP, and 0.25 μM biotin-GGLFDDPSYVN-VQNL-$NH_2$ (SEQ ID NO: 2) peptide substrate. Each of the above compounds displayed an $IC_{50}$ value of less than 10 μM with respect to FLT-1, VEGFR2, VEGFR3, and FGFR1.

Recombinant and active tyrosine kinases Fyn, and Lck are available commercially and were purchased from Upstate Biotechnology. For each assay, test compounds were serially diluted in DMSO and then mixed with an appropriate kinase reaction buffer plus 10 nM $^{33}P$ gamma-labeled ATP. The kinase protein and the appropriate biotinylated peptide substrate were added to give a final volume of 150 μL. Reactions were incubated for 3-4 hours at room temperature and then stopped by transferring to a streptavidin-coated white microtiter plate (Thermo Labsystems) containing 100 μL of stop reaction buffer of 100 mM EDTA and 50 μM unlabeled ATP. After 1 hour incubation, the streptavidin plates were washed with PBS and 200 μL Microscint 20 scintillation fluid was added per well. The plates were sealed and counted using TopCount. The concentration of each compound for 50% inhibition ($IC_{50}$) was calculated employing non-linear regression using XL Fit data analysis software.

The kinase reaction buffer for Fyn, Lck, and c-ABL contained 50 mM Tris-HCl pH 7.5, 15 mM $MgCl_2$, 30 mM $MnCl_2$, 2 mM DTT, 2 mM EDTA, 25 mM beta-glycerol phosphate, 0.01% BSA/PBS, 0.5 μM of the appropriate peptide substrate (biotinylated Src peptide substrate: biotin-GGGGKVEKIGEGTYGVVYK-$NH_2$ (SEQ ID NO: 3) for Fyn and Lck), 1 μM unlabeled ATP, and 1 nM kinase.

The kinase activity of c-Kit and FLT-3 were measured by providing ATP and a peptide or protein containing a tyrosine amino acid residue for phosphorylation, and assaying for the transfer of phosphate moiety to the tyrosine residue. Recombinant proteins corresponding to the cytoplasmic domains of the c-Kit and FLT-3 receptors were purchased (Proquinase). For testing, an exemplary compound, for example 4-amino-5-fluoro-3-[5-(4-methylpiperazin-1-yl)-1H-benzimidazol-2-yl]quinolin-2(1H)-one, was diluted in DMSO and then mixed with the kinase reaction buffer described below plus ATP. The kinase protein (c-Kit or FLT-3) and the biotinylated peptide substrate (biotin-GGLFDDPSYVNVQNL-NH2 (SEQ ID NO: 2)) were added to give a final volume of 100 μL. These reactions were incubated for 2 hours at room temperature and then stopped by addition of 50 μL of 45 mM EDTA, 50 mM HEPES, pH 7.5. The stopped reaction mixture (75 μL) was transferred to a streptavidin-coated microtiter plate (Boehringer Mannheim) and incubated for 1 hour. Phosphorylated peptide product was measured with the DELPHIA time-resolved fluorescence system (Wallac or PE Biosciences), using a Europium-labeled anti-phosphotyrosine antibody, PT66, with the modification that the DELFIA assay buffer was supplemented with 1 mM $MgCl_2$ for the antibody dilution. Time resolved fluorescence values were determined on a Wallac 1232 DELFIA fluorometer or a PE Victor II multiple signal reader. The concentration of each compound for 50% inhibition ($IC_{50}$) was calculated employing non-linear regression using XL Fit data analysis software.

FLT-3 and c-Kit kinases were assayed in 50 mM Hepes pH 7.5, 1 mM NaF, 2 mM $MgCl_2$, 10 mM $MnCl_2$ and 1 mg/mL BSA, 8 μM ATP and 1 μM of corresponding biotinylated peptide substrate (biotin-GGLFDDPSYVNVQNL-$NH_2$ (SEQ ID NO: 2)). The concentration of FLT-3 and c-Kit kinases were assayed at 2 nM.

$IC_{50}$s were measured for the metabolites of compound 1 and are shown in Table 3 along with $IC_{50}$s of compound 1 for comparison.

TABLE 3

| | $IC_{50}$ (μM) | | | | | |
|---|---|---|---|---|---|---|
| Compound | VEGFR flt | VEGFR flk1 | bFGFR | PDGFR | Flt3 | c-kit |
| Compound 1 | 0.010 | 0.013 | 0.008 | 0.027 | 0.0001 | 0.0015 |
| Compound 2 | 0.004 | 0.009 | 0.005 | 0.010 | 0.0004 | 0.0002 |
| Compound 3 | 0.019 | 0.012 | 0.019 | 0.037 | 0.0001 | 0.0002 |

Example 4

This single agent study evaluated daily oral dosing of compound 1 in the KM12L4a human colon tumor model.

Female Nu/Nu mice, aged 7-8 weeks (Charles River), were implanted with $2\times10^6$ KM12L4a cells subcutaneously in the right flank. Treatment began 7 days later when average tumor volume was 125 $mm^3$. This was designated as study day 1. Compound 1 was formulated as a solution in 10 mM $H_3PO_4$ and administered by oral gavage.

Seven treatment groups were included in the study, (n=10/group): vehicle (water) p.o., q.d.; and six groups of compound 1 doses: 3, 10, 30, 100, 200, 300 mg/kg p.o., q.d.

Plasma samples were drawn from satellite animals in each dose group on various days to characterize the pharmacokinetics of compound 1 in tumor-bearing mice (N=2/timepoint/dose group). Tissue and tumor concentrations of compound 1 were determined in samples collected from animals in the 100 and 200 mg/kg dose group at 8 and 24 hours post-dose on Day 22 (N=2/timepoint/dose group).

Plasma compound 1 concentrations were determined by a non-validated LC/MS/MS assay with a calibration range of 1 to 8000 ng/mL and a lower limit of quantitation (LLOQ) of 1 ng/mL (Charles River Laboratories, Worcester, Mass. Tissue and tumor compound 1 concentrations were also determined using a non-validated LC/MS/MS assay with a calibration range of 20 to 43740 ng/g and a LLOQ of 20 ng/g.

Composite pharmacokinetic parameters ($C_{max}$ and AUC) were obtained using standard noncompartmental analysis from mean plasma compound concentration-time data in each dose group on each sampling day (WinNonlin Professional, version 4). The reported AUC values were determined using 3 concentration-time data points. Predose concentration values were reported as those observed immediately prior to dosing.

Significant dose-dependent inhibition in tumor growth was observed at all doses by 4-7 days of treatment (see Table 4). The calculated $ED_{50}$ was 17 mg/kg. Tumor regressions of >50% of initial size were observed in the majority of mice dosed with compound 1 at 200 and 300 mg/kg, however these doses were not tolerated for the entire study duration. By days 12-16, mice treated with 300 mg/kg lost 20-30% body weight and were euthanized. In those treated with 200 mg/kg, 1 of 10 was euthanized on day 14 with 22% wt loss, and the remaining mice were euthanized days 21-24 with >25% weight loss. Mice were dosed for 37 days with 100 mg/kg and remained at 98% of initial weight; tumors remained stable at this dose (FIG. 1). The vehicle group was taken down on day 9, and tumor growth inhibition (TGI) was calculated. (Table 4).

TABLE 4

Dose response activity of Compound 1

| Daily dose compound 1 (n = 9-10/gp) | Tumor Vol Day 9 Mean ± SD (mm³) | Treated/ Control | % Tumor Growth Inhibition | P value vs. Vehicle |
|---|---|---|---|---|
| Vehicle | 1333 ± 283 | — | — | — |
| 3 mg/kg | 1168 ± 202 | 0.88 | 12 | 0.1519 |
| 10 mg/kg | 861 ± 321 | 0.65 | 35 | 0.0037 |
| 30 mg/kg | 553 ± 213 | 0.42 | 58 | ≦0.00001 |
| 100 mg/kg | 263 ± 108 | 0.20 | 80 | ≦0.00001 |
| 200 mg/kg | 98 ± 40 | 0.07 | 93 | ≦0.00001 |
| 300 mg/kg | 74 ± 30 | 0.06 | 94 | ≦0.00001 |

On the second day of dosing (Day 2), plasma concentrations of compound 1 increased proportionally with dose (Table 5) in all dosing groups. Following multiple dosing for at least 2 weeks, plasma concentrations were comparable to those on Day 2, suggesting no accumulation upon once daily dosing in mice (Table 5). Similarly, predose plasma concentration of compound 1 collected on Days 3, 8, and 15 were similar within each dose group, suggesting that steady state was reached after Day 2. Therefore, these data suggest that compound 1 follows dose-and time-independent pharmacokinetics in tumor-bearing mice.

Figure 2:
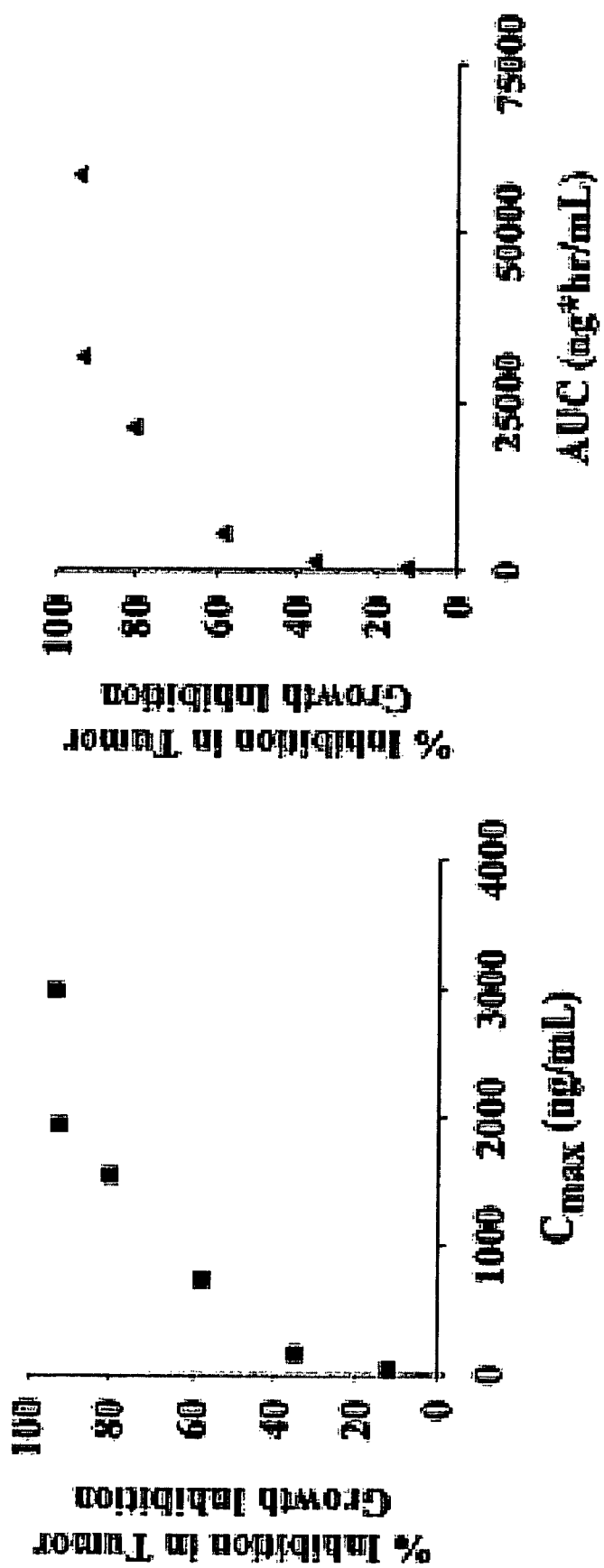
FIG. 2 shows the $C_{max}$ and AUC values versus percent inhibition of KM12L4a tumor growth in KM12L4a tumor-bearing mice.

Tumor growth inhibition of 35-60% was observed at doses of 10 and 30 mg/kg, respectively. The corresponding plasma exposure of compound 1, as assessed by $C_{max}$ and AUC values, ranged from 163-742 ng/mL and 1420-5540 ng*hr/mL, respectively (FIG. 2). The corresponding plasma predose concentration values ranged from 2-135 ng/mL.

TABLE 5

Composite Compound 1 Pharmacokinetic Parameters and Plasma Concentrations-Time Data Following Once-Daily Oral Dosing of Compound 1 to Mice Bearing SC KM1214a Tumors

| Dose (mg/kg/day) | Day | Composite Pharmacokinetic Parameters | | Mean Plasma Concentrations (ng/mL) | | | |
|---|---|---|---|---|---|---|---|
| | | $C_{max}$ (ng/mL) | AUC (ng * hr/mL)[1] | Time (hr) | | | |
| | | | | 0* | 2 | 8 | 24* |
| 3 | 2 | 48 | 420 | | 48.0 | 12.7 | 11.1 |
| | 8 | — | — | 1.55 | | | |
| 10 | 2 | 163 | 1420 | | 163 | 67.3 | 2.72 |
| | 8 | — | — | 2.37 | | | |
| | 15 | — | — | 3.95 | | | |
| | 17 | — | — | | | 136 | 65.8 |
| 30 | 2 | 742 | 5540 | | 742 | 228 | 8.42 |
| | 8 | — | — | 7.37 | | | |
| | 15 | — | — | 23.7 | | | |
| | 17 | — | — | | | 416 | 123 |
| 100 | 2 | 1560 | 18500 | | 1560 | 1050 | 97.8 |
| | 8 | — | — | 135 | | | |
| | 15 | — | — | 54.7 | | | |
| | 22 | 1550 | 21200 | | 1550 | 1330 | 47.7 |
| 200 | 2 | 2500 | 47200 | | 2370 | 2500 | 1270 |
| | 8 | — | — | 454 | | | |
| | 15 | — | — | 434 | | | |
| | 22 | 1940 | 31600 | | 1940 | 1400 | 1050 |
| 300 | 2 | 3450 | 61300 | | 3450 | 2900 | 1950 |
| | 8 | — | — | 911 | | | |
| | 15 | — | — | 1220 | | | |
| | 18 | 2980 | 58400 | | 2440 | 2250 | 2980 |

[1]AUC calculated from 3 concentration-time data pairs
— Not determined
*Predose concentrations Tissue concentrations of compound 1 on Day 22 were higher than those in plasma in the 100 and 200 mg/kg dose groups at each of the two sampling times (8 and 24 hours postdose) (Table 6). Brain or heart concentrations of compound 1 were 13- to 34-fold higher than those in plasma; whereas liver, lung, and kidney concentrations were 40- to 126-fold higher than those in plasma at 8 or 24 hours postdose in these two dose groups. In general, the ratio of tissue-to-plasma concentrations at 8 hours was comparable to that at 24 hours. Furthermore, tissue concentrations at 24 hours were consistently lower compared to those at 8 hours. Taken together, these results suggest that tissue concentrations of compound 1 appeared to decline in parallel with those in plasma. Therefore, compound 1 appears to be widely distributed into tissues (including brain) relative to plasma but does not accumulate in tissues following multiple oral dosing.

TABLE 6

Mean Tissue, Tumor and Plasma Concentrations on Day 22 Following Once-Daily Oral Administration of 100 or 200 mg/kg/day compound 1 to KM12L4a Tumor-Bearing Mice

| Dose (mg/kg) | Time (hr) | Tissue Concentrations (ng/g) | | | | | Plasma Conc (ng/mL) |
|---|---|---|---|---|---|---|---|
| | | Brain | Heart | Kidney | Liver | Lung | Tumor | |
| 100 | 8 | 16900 | 24700 | 83700 | 107000 | 87500 | 48500 | 1330 |
| | 24 | 675 | 1630 | 3900 | 5080 | 3170 | 16900 | 47.7 |
| 200 | 8 | 24200 | 40400 | 143000 | 176000 | 277000 | 107000 | 1400 |
| | 24 | 9160 | 18700 | 82800 | 109000 | 41600 | 87900 | 1050 |

N = 2/timepoint/dose group, except in the 200 mg/kg at 24 hr, where N = 1

Tumor compound 1 concentrations on Day 22 were 37- to 354-fold higher than those in plasma in the 100 and 200 mg/kg dose groups at each of the two sampling times (8 and 24 hours postdose). However, tumor concentrations at 24 hours were only 17 to 65% lower than those at 8 hours postdose in these two dose groups suggesting a somewhat slower elimination rate from tumors compared to that from other normal tissues (such as, brain, heart, liver, lung, and kidneys). Therefore, compound 1 appears to be extensively distributed to tumors relative to plasma but may exhibit preferential retention in tumor relative to plasma or normal tissues.

In summary, the efficacy and tolerability of compound 1 was dose related, with significant inhibitions after 4 to 7 days of treatment. Tumor regressions were observed at 300 and 200 mg/kg; these doses were tolerated daily for approximately 14 and 21 days, respectively. Weight loss was the clinical sign associated with toxicity. Doses of 100 mg/kg were tolerated for 37 days with no adverse clinical signs, with tumor growth inhibition of 80% compared to control. 30 mg/kg inhibited growth by 60%. Compound 1 demonstrated dose- and time-independent pharmacokinetics in tumor-bearing mice. Plasma compound 1 $C_{max}$, AUC, and $C_{min}$ values associated with 35-60% tumor growth inhibition ranged from 163-742 ng/mL, 1420-5540 ng*hr/mL, and 2-135 ng/mL, respectively. Compound 1 was distributed widely to tissues, however did not appear to accumulate in tissues following multiple oral dosing. There was a trend towards preferential retention of compound 1 in tumors relative to other tissues following oral dosing.

Example 5

This single agent study evaluated intermittent oral dosing of compound 1 in the PC3 human prostate tumor model.

Male SCID mice, aged 9-10 weeks, were implanted with 5 million PC3 human prostate cells subcutaneously in the flank. Treatment began when tumors reached 150 mm³. This was designated as study day 1. Compound 1 was formulated as an aqueous solution and administered by oral gavage.

Five treatment groups were included in the study, (n=10/group): Vehicle (water) p.o., q.d.; and four groups of compound 1 doses of 100 mg/kg q.d., q.2.d., q.3.d., q.4.d.

As shown in Table 7 significant and similar tumor inhibition results were observed in all treatment groups. The study was suspended for the daily dosing group on day 11. The study was terminated on study day 25 for the remaining groups and mean tumor volume was measured and compared to vehicle. As a clinical indication of toxicity percentage weight loss was measured for each group.

TABLE 7

| Group | n | Total doses compound 1 | Mean Tumor Volume day 25 | % TGI vs. vehicle | Mean % Wt. loss (range) |
|---|---|---|---|---|---|
| Vehicle | 10 | | 2011 | | 13 (1-24%) |
| 100 mpk q d, days 1-11 | 8 | 11 | 790 | 60% | 12 (3-35%) |
| 100 mpk q 2 days | 10 | 13 | 507 | 75% | 4 (0-13%) |
| 100 mpk q 3 days | 10 | 9 | 645 | 68% | 4 (0-11%) |
| 100 mpk q 4 days | 9 | 7 | 686 | 66% | 10 (5-17%) |

Example 6

To confirm the structures of the identified metabolites of compound 1, the metabolites were independently synthesized.

Compound 2, the N-oxide metabolite of compound 1, was synthesized as shown in the scheme below. Compound 1 was heated in a mixture of ethanol, dimethylacetamide and hydrogen peroxide. Upon completion of the reaction, compound 2 was isolated by filtration and washed with ethanol. If necessary, the product could be further purified by column chromatography.

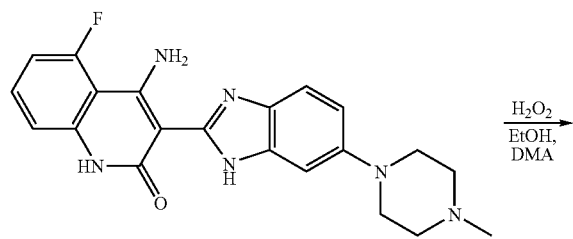

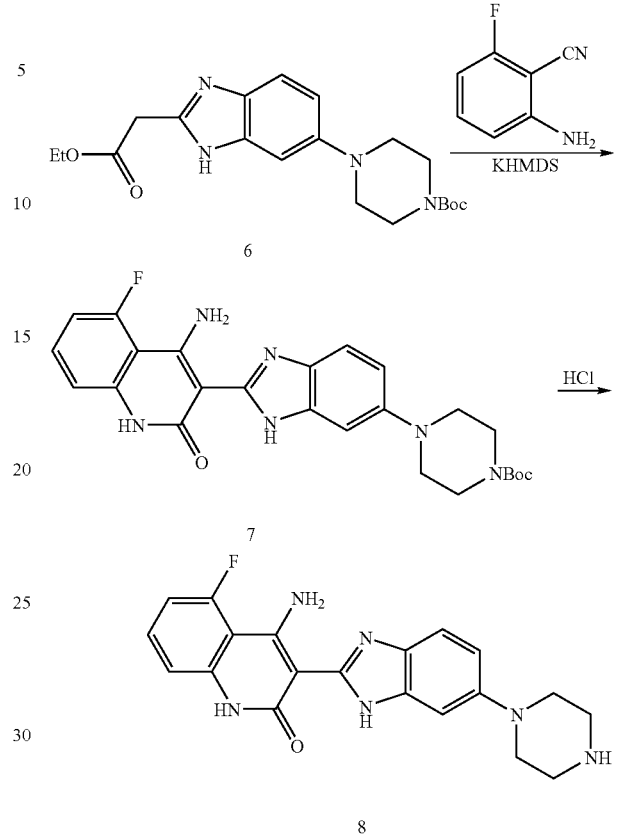

Compound 3, the N-desmethyl metabolite of compound 1, was synthesized as shown in the scheme below. 5-Chloro-2-nitroaniline was treated with piperazine to yield 4 which was subsequently protected with a butyloxycarbonyl (Boc) group to yield 5. Reduction of the nitro group followed by condensation with 3-ethoxy-3-iminopropionic acid ethyl ester gave 6. Condensation of 6 with 6-fluoroanthranilonitrile using potassium hexamethyldisilazide as the base yielded 7. Crude 7 was treated with aqueous HCl to yield the desired metabolite as a yellow/brown solid after purification.

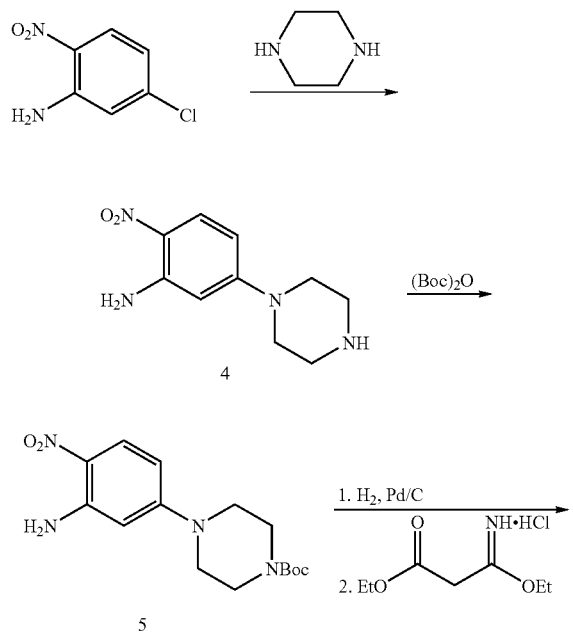

Example 7

Preparation of Lactic Acid Salt of Compound 1

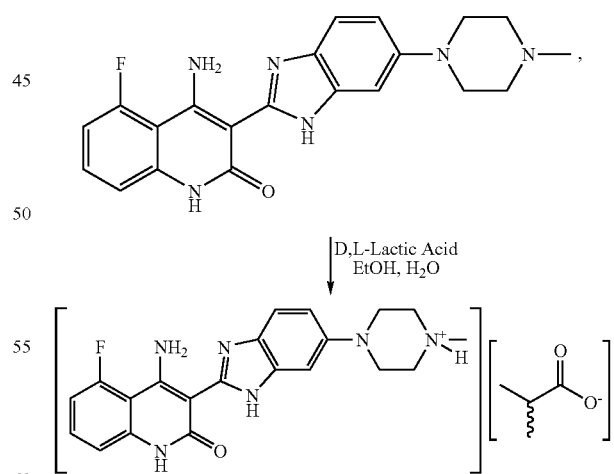

A 3000 mL 4-necked jacketed flask was fitted with a condenser, a temperature probe, a $N_2$ gas inlet, and a mechanical stirrer. The reaction vessel was purged with $N_2$ for at least 15 minutes and then charged with 4-amino-5-fluoro-3-[6-(4-methyl-piperazin-1-yl)-1H-benzimidazol-2-yl]-1H-quinolin-2-one (484 g, 1.23 mol). A solution of D,L-Lactic acid (243.3 g, 1.72 mol of monomer-see the following paragraph), water (339 mL), and ethanol (1211 mL) was prepared and then charged to the reaction flask. Stirring was initiated at a medium rate, and the reaction was heated to an internal temperature of 68-72° C. The internal temperature of the reaction was maintained at 68-72° C. for 15-45 minutes and then heating was discontinued. The resulting mixture was filtered through a 10-20 micron frit collecting the filtrate in a 12 L flask. The 12 L flask was equipped with an internal temperature probe, a reflux condenser, an additional funnel, a gas inlet an outlet, and an overhead stirrer. The filtrate was then stirred at a medium rate and heated to reflux (internal temperature of about 78° C.). While maintaining a gentle reflux, ethanol (3,596 mL) was charged to the flask over a period of about 20 minutes. The reaction flask was then cooled to an internal temperature ranging from about 64-70° C. within 15-25 minutes and this temperature was maintained for a period of about 30 minutes. The reactor was inspected for crystals. If no crystal were present, then crystals of the lactic acid salt of 4-amino-5-fluoro-3-[6-(4-methyl-piperazin-1-yl)-1H-benzimidazol-2-yl]-1H-quinolin-2-one (484 mg, 0.1 mole %) were added to the flask, and the reaction was stirred at 64-70° C. for 30 minutes before again inspecting the flask for crystals. Once crystals were present, stirring was reduced to a low rate and the reaction was stirred at 64-70° C. for an additional 90 minutes. The reaction was then cooled to about 0° C. over a period of about 2 hours, and the resulting mixture was filtered through a 25-50 micron fritted filter. The reactor was washed with ethanol (484 mL) and stirred until the internal temperature was about 0° C. The cold ethanol was used to wash the filter cake, and this procedure was repeated 2 more times. The collected solid was dried to a constant weight at 50° C. under vacuum in a vacuum oven yielding 510.7 g (85.7%) of the crystalline yellow lactic acid salt of 4-amino-5-fluoro-3-[6-(4-methyl-piperazin-1-yl)-1H-benzimidazol-2-yl]-1H-quinolin-2-one. A rubber dam or inert conditions were typically used during the filtration process. While the dry solid did not appear to be very hygroscopic, the wet filter cake tends to pick up water and become sticky. Precautions were taken to avoid prolonged exposure of the wet filter cake to the atmosphere.

Commercial lactic acid generally contains about 8-12% w/w water, and contains dimers and trimers in addition to the monomeric lactic acid. The mole ratio of lactic acid dimer to monomer is generally about 1.0:4.7. Commercial grade lactic acid may be used in the process described in the preceding paragraph as the monolactate salt preferentially precipitates from the reaction mixture. Lactic acid monomer is purified according to the following procedure.

Example 8

This study evaluated the antiangiogenic potential of compound 1 in the FGF supplemented Matrigel model.

Female BDF1 mice, aged 11-12 weeks (Charles River, Wilmington, Mass.), were subcutaneously implanted with 0.5 mL Matrigel (BD Biosciences, Bedford, Mass.) supplemented with 2 μg FGF-2. The FGF-2 supplemented blood vessel formation (neovascularization or angiogenesis) was quantified by measuring hemoglobin levels in the Matrigel plugs following their removal from the animals.

Oral administration of test article began one day prior to Matrigel implantation and continued once daily for eight doses. Compound 1 was formulated as a solution in 10 mM $H_3PO_4$. Twelve treatment groups were included: vehicle (10 mM $H_3PO_4$) p.o., q.d.×8 days (2 control groups; mice implanted with unsupplemented Matrigel (baseline hemoglobin level) or FGF-supplemented Matrigel (positive control); compound 1 dosed at 3, 10, 30, 100, 200, 300 mg/kg p.o., q.d.×8 days. There were 8 mice per group, except for mice dosed at 200 and 300 mg/kg, which were 4 per group.

Percent inhibition of hemoglobin levels in compound-treated mice compared to mice treated with vehicle indicates the antiangiogenic potency of the compound. Results are expressed as total hemoglobin (mg/dL) per Matrigel plug. The $ED_{50}$ is defined as the dose that effectively inhibits angiogenesis by approximately 50%. Hemoglobin concentrations were determined in homogenized Matrigel plugs removed from mice and flash frozen, using absorbance spectroscopy with Drabkin's reagent (Sigma Diagnostics, St. Louis Mo.).

To evaluate plasma exposures of compound 1, blood was collected 2 and 24 hours after 8 consecutive doses (Day 8). In the 200 and 300 mg/kg dose groups, blood was collected only at the 2 hour timepoint. Plasma concentrations of 1 were determined by a non-validated LC/MS/MS assay with a calibration range of 1 to 8000 ng/mL and a lower limit of quantitation (LLOQ) of 1 ng/mL (Charles River Laboratories, Worcester, Mass.).

On Day 8, hemoglobin levels in Matrigel plugs and plasma concentrations of compound 1 were measured. Animals were observed and body weights were measured throughout the study.

Compound 1 resulted in significant inhibition of hemoglobin concentration in Matrigel plugs at each dose evaluated compared to plugs from vehicle treated animals (Table 8). The calculated $ED_{50}$ was 2.6 mg/kg. The 3 and 10 mg/kg doses resulted in 54% and 57% inhibition, respectively, whereas the 30, 100, 200 and 300 mg/kg doses reduced hemoglobin to the level of unsupplemented Matrigel, resulting in 70-92% inhibition vs. FGF-supplemented controls. The plasma concentrations of compound 1 at 2 hours post dose on day 8, showed a dose proportional increase with concentrations ranging from 44 ng/mL at 3 mg/kg to 3920 ng/mL at 300 mg/kg (Table 9). All doses were well tolerated and no weight loss was observed.

TABLE 8

Hemoglobin Concentrations and Dose Dependent Reduction in Hb Concentrations in Matrigel Plugs Inhibition in Matrigel Following Oral Administration of Compound 1

| Treatment | n | Mean Hb ± SD mg/dL | % Hb inhibition vs. Vehicle treatment of Matrigel + FGF | p value t-test vs. vehicle treatment Matrigel FGF |
|---|---|---|---|---|
| Matrigel alone | 8 | 26 ± 15 | | |
| Matrigel FGF + Vehicle | 8 | 69 ± 34 | | |
| 300 mg/kg 1 | 4 | 6 ± 0.8 | 91% | 0.005 |
| 200 mg/kg 1 | 4 | 8 ± 0.3 | 89% | 0.004 |
| 100 mg/kg 1 | 8 | 14 ± 7 | 80% | <0.0005 |
| 30 mg/kg 1 | 8 | 20 ± 8 | 71% | <0.0005 |
| 10 mg/kg 1 | 8 | 29 ± 16 | 58% | 0.010 |
| 3 mg/kg 1 | 8 | 32 ± 14 | 54% | 0.012 |

TABLE 9

Plasma Concentrations of Compound 1 Measured After 8 Consecutive Doses

| Compound 1 Dose (mg/kg/day) | Mean Plasma Conc @ 2 hr# (ng/mL) | Mean Plasma Conc @ 24 hr# (ng/mL) |
|---|---|---|
| 3 | 44 | $0^a$ |
| 10 | 123 | $0^a$ |
| 30 | 339 | 1.4 |

TABLE 9-continued

Plasma Concentrations of Compound 1 Measured After 8 Consecutive Doses

| Compound 1 Dose (mg/kg/day) | Mean Plasma Conc @ 2 hr# (ng/mL) | Mean Plasma Conc @ 24 hr# (ng/mL) |
|---|---|---|
| 100 | 954 | 24 |
| 200 | 1910 | NS |
| 300 | 3920 | NS |

$^a$Plasma concentrations below lower limit of quantitation ($\leq$1 ng/mL)
NS = No samples were collected
samples collected 2 hours and 24 hours after dosing Plasma concentrations of 1 (2 hr postdose) increased proportionally with dose. A dose and plasma concentration dependent reduction in hemoglobin content of Matrigel plugs was observed. Plasma concentrations (2 hr postdose, Day 8) of 44 ng/mL appear to be associated with antiangiogenic activity in this model.

In summary, the hemoglobin inhibition of compound 1 was dose-dependent, with significant inhibition after 8 days of treatment. Statistically significant hemoglobin inhibition was observed with all doses of compound 1. All doses were well tolerated with no weight loss or adverse clinical signs observed. Compound 1 plasma concentrations (2 hr postdose) of 44 ng/mL were associated with antiangiogenic activity in this model.

Example 9

The metabolite profile of compound 1 in monkey plasma from a 5 mg/kg BID multiple oral dose study was determined in dose day 1 and 14 samples. One metabolite was identified and characterized by LC/UV and LD/MS/MS resulting from demethylation (compound 3). Parent (P) compound 1 produced an M+H$^+$ ion at m/z=393.3 with a chromatographic retention time of 18.3 minutes. The demethylated metabolite (P—CH$_3$) was identified with an m/z=379.3 (M+H$^+$) and a chromatographic retention time of 18.1 min. The mass difference of 14 daltons between the metabolite and compound 1 is consistent with a demethylated compound 1. The mass and chromatographic retention of the metabolite was identical to independently synthesized compound 3. The metabolite corresponding to the piperazine N-oxide of compound 1 (N-oxide compound 2) was not detected in plasma at this dose level. The components producing a UV signal at 17.7 and 18.5 minutes in the absorbance chromatogram at 356 nm were determined to be matrix components and not metabolites based on the UV spectral comparisons to compound 1 and due to their presence in blank plasma (time 0 dose day 1).

The estimated levels of the demethylated metabolite are given in Table 1. The estimated levels of metabolites (in compound 1 equivalents) are based on UV absorbance peak height ratios of metabolite to that of compound 1 obtained in this analysis and extrapolated by factoring the absorbance ratio to the known levels of compound 1 determined in the same samples in a previous qantitative analytical study. It was found that parent compound was in greater abundance than the metabolite at all pooled time points. The levels of compound 1 were found to be substantially lower in the day 14 samples in parallel with the N-desmethyl metabolite which was essentially undetectable. No other metabolites including conjugated Phase II type metabolites (glucuronide or sulphate) were detected in these plasma samples on day 1 or 14 of dose administration.

TABLE 10 compound 1 levels and estimated compound 1 metabolite levels in rat plasma (N = 2) with multiple oral doses of compound 1 (5 mg/kg, BID).

| Dose (mg/kg/day)$^a$ | Day | Pooled Sample Time (hr) | (P-CH$_3$) (ng/ml)$^b$ | compound 1 (ng/ml)$^c$ |
|---|---|---|---|---|
| 10 | 1 | 0 | 0 | 0 |
| 10 | 1 | 1, 2 | 8.5 | 28 |
| 10 | 1 | 4, 8 | 31 | 62 |
| 10 | 1 | 12, 13, 14, 16, 20, 24 | 10 | 21 |
| 10 | 14 | 0 | ND | 2 |
| 10 | 14 | 1, 2 | ND | 4.2 |
| 10 | 14 | 4, 8 | ND | 2.2 |
| 10 | 14 | 12, 13, 14, 16, 20, 24 | ND | 3.2 |

$^a$Rats were dosed with 5/mg/kg compound 1 BID in 12 hour intervals (T = 0 and T = 12 hours).
$^b$Metabolite levels estimated based on metabolite/compound 1 UV response ratios obtained in this study and factored by the known compound 1 levels previously determined in a separate quantitative study.
$^c$Compound 1 levels presented in this table are averaged values of previously quantified levels from a separate study.
ND: Non detectable

Example 10

Studies with plasma and tumors collected from mice following treatment with compound 1 were performed to evaluate potential pharmacodynamic endpoints. Analysis of target modulation in KM12L4a tumors after compound 1 treatment indicated that phosphorylation of VEGFR1, VEGFR2, PDGFRβ, and FGFR1 were inhibited in a time- and dose-dependent manner. For example, HMVEC cells showed inhibition of VEGF mediated VEGFR2 phosphorylation with an IC$_{50}$ of about 0.1 μM. In addition, treatment of endothelial cells with compound 1 inhibited MAPK and Akt phosphorylation mediated by VEGF.

Furthermore, a time- and dose-dependent inhibition of ERK (MAPK) activation, a downstream target of receptor tyrosine kinases, was observed with IC$_{50}$s ranging from 0.1 to 0.5 μM in KM12L4A cells. (KM12L4A cells express PDGFRβ and VEGFR1/2 on their surfaces.) KM12L4A cells were incubated 3 h with compound 1 in serum-free DMEM. After the harvest, lysates were separated by SDS-Page and probed with the phosphor-ERK1/2 and ERK1/2 antibodies. For detection, ECL reagents (Amersham) were used. The inhibitory effects of compound 1 on receptor phosphorylation and ERK activation were maintained for 24 hours after treatment. Phosphorylation of ERK1/2 in MV4-11 cells was inhibited by 1 at IC$_{50}$s of 0.01 to 0.1 μM in a dose-dependent manner.

Significant activity was observed in vivo in the HCT116 human colon tumor model. In HCT116 tumors, compound 1 inhibited the phosphorylation of ERK (MAPK) in a dose- and time-dependent manner and significant changes in histology analyses of the tumors was observed.

These PK/PD evaluations in preclinical models indicate that compound 1 showed a dose- and time-dependent inhibition of both the target receptors and the downstream signaling molecule, ERK (MAPK). These studies will aid in the identification of potential biomarkers to support the monitoring of biological activity of compound 1 in clinical trials.

Example 11

The distribution of radioactivity in tissues after administration of a single oral (PO) dose (5 mg/kg) of $^{14}$C-labeled compound 1 (at 4-position of quinolinone ring) to male and female Sprague Dawley (SD) rats was determined by whole-body autoradiography (WBA). Blood and carcasses for WBA were collected at specified time points through 24 hours post-dose. Carcasses were frozen in a hexane/dry ice bath, drained, blotted dry, and placed on dry ice or stored at approximately −70° C. for at least 2 hours. The frozen carcasses were embedded in chilled carboxymethylcellulose, frozen into blocks along with embedded autoradiographic standards, and stored at −20° C. until analysis. Appropriate sections of 40 μm thickness were collected on adhesive tape at 5 levels of interest in the sagital plane. All major tissues, organs and biological fluids were represented. Phosphorimaging screens were exposed to the sections and scanned and a standard curve created for interpolating tissue concentrations of $^{14}$C-1. Plasma was analyzed for concentration of radioactivity by liquid scintillation counting (LSC). Illustrative results are presented in Table 11.

Following oral administration of $^{14}$C-1, radioactivity derived from $^{14}$C-1 was widely distributed throughout all tissues by 1 hour postdose, and had reached $C_{max}$ in most tissues by 4 hours postdose. Overall distribution of radioactivity in the tissues of males and females was similar. $^{14}$C-1-derived radioactivity was cleared more slowly from tissues than from plasma. In males and females, the highest tissue concentrations of $^{14}$C-1, excluding the gastrointestinal tract through 24 hours were detected in the harderian gland, adrenal gland, renal medulla, intra-orbital lacrimal gland, and exorbital lacrimal gland. $^{14}$C-1-derived radioacitivity crossed the blood/brain barrier after oral dose administration.

TABLE 11

Tissue:plasma concentration ratios determined by whole-body autoradiography at specified times following a single oral dose of Compound 1 (5 mg/kg) to male rats

| | Tissue:Plasma Concentration Ratios Animal Number (Sacrifice Time) | | | |
|---|---|---|---|---|
| Tissue | 1 (1 Hour) | 2 4 (Hours) | 3 (10 Hours) | 4 (24 Hours) |
| Adrenal gland | 34.3 | 33.5 | 56.0 | 68.8 |
| Blood | 1.84 | 1.04 | 1.35 | 1.06 |
| Bone | 0.826 | 0.679 | 1.00 | 1.23 |
| Bone marrow | 13.8 | 23.3 | 29.7 | 26.9 |
| Cecum | 16.9 | 11.3 | 23.7 | 15.9 |
| Cecum contents | 0.484 | 15.7 | 356 | 130 |
| Cerebellum | 4.86 | 2.63 | 2.47 | 1.51 |
| Cerebrum | 6.16 | 3.39 | 3.21 | 1.71 |
| Cerebral spinal fluid (CSF) | 13.7 | 18.0 | 24.0 | 11.5 |
| Diaphragm | 14.1 | 9.00 | 12.2 | 6.49 |
| Epididymis | 3.61 | 6.57 | 9.05 | 8.53 |
| Esophageal contents | 2.90 | 6.82 | 1.08 | 1.15 |
| Esophagus | 98.1 | 17.7 | 12.3 | 7.26 |
| Exorbital lacrimal gland | 17.0 | 28.9 | 39.2 | 59.9 |
| Eye | 0.535 | 1.01 | 1.20 | 1.51 |
| Fat (abdominal) | 3.08 | 1.89 | 2.04 | 1.44 |
| Fat (brown) | 16.2 | 20.2 | 16.2 | 8.85 |
| Harderian gland | 14.3 | 34.2 | 128 | 300 |
| Intra-orbital lacrimal gland | 16.3 | 30.4 | 42.4 | 63.0 |
| Kidney | 45.1 | 32.4 | 49.1 | 24.3 |
| Large intestinal contents | NA | 7.00 | 454 | 238 |
| Large intestine | 11.6 | 12.8 | 21.8 | 10.9 |
| Liver | 121 | 48.9 | 45.0 | 44.7 |
| Lung | 47.2 | 26.9 | 28.8 | 16.8 |
| Medulla | 4.08 | 2.76 | 2.88 | 1.51 |
| Muscle | 5.93 | 4.64 | 5.77 | 2.64 |
| Myocardium | 16.8 | 11.5 | 11.8 | 4.62 |
| Nasal turbinates | 4.44 | 6.29 | 11.9 | 11.0 |
| Olfactory lobe | 3.77 | 2.27 | 2.15 | 1.15 |
| Pancreas | 25.7 | 20.5 | 29.3 | 10.5 |
| Pineal gland | 23.0 | NA | NA | NA |
| Pituitary gland | 20.5 | 33.9 | 48.1 | 21.5 |
| Preputial gland | NA | NA | 23.3 | 41.3 |
| Prostate | 7.29 | 11.4 | 14.2 | 11.2 |

NA Not applicable.

It is understood that the invention is not limited to the embodiments set forth herein for illustration, but embraces all such forms thereof as come within the scope of the following claims.

What is claimed is:

1. A method for alleviating the symptoms of or halting the progression or worsening of the symptoms of cancer, wherein the cancer is selected from the group consisting of gastrointestinal stromal cancer, glioma, melanoma, bladder cancer and renal cancer, comprising administering to a subject having said cancer a sufficient amount of a compound having the formula:

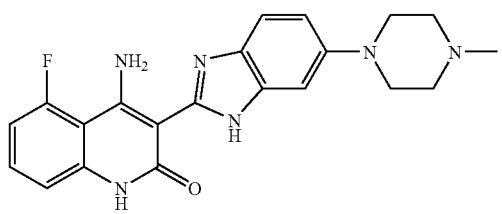

a pharmaceutically acceptable salt thereof, a tautomer thereof, or a pharmaceutically acceptable salt of the tautomer to provide a maximum concentration ($C_{max}$) of 20 to 4000 ng/mL of the compound in the subject's plasma or a $C_{max}$ of 40 to 8000 ng/mL of the compound in the subject's blood.

2. The method of claim 1, wherein the amount of the compound is sufficient to provide a $C_{max}$ of 50 to 500 ng/mL of the compound in the subject's plasma or a $C_{max}$ of 100 to 1000 ng/mL of the compound in the subject's blood.

3. The method of claim 1, wherein the amount of the compound is sufficient to provide a $C_{max}$ of 50 to 250 ng/mL of the compound in the subject's plasma or a $C_{max}$ of 100 to 500 ng/mL of the compound in the subject's blood.

4. The method of claim 1, wherein the amount of the compound is sufficient to provide a $C_{max}$ of 75 to 150 ng/mL of the compound in the subject's plasma or a $C_{max}$ of 150 to 300 ng/mL of the compound in the subject's blood.

5. The method of claim 1, wherein the amount of the compound is sufficient to provide a $C_{max}$ of 100 to 2000 ng/mL of the compound in the subject's plasma or a $C_{max}$ of 200 to 4000 ng/mL of the compound in the subject's blood.

6. The method of claim 1, wherein the amount of the compound is sufficient to provide a $C_{max}$ of 100 to 1000 ng/mL of the compound in the subject's plasma or a $C_{max}$ of 200 to 2000 ng/mL of the compound in the subject's blood.

7. The method of claim 1, wherein the lactate salt of the compound is administered to the subject and the subject is a human.

8. The method of claim 7, wherein the lactate salt is in an aqueous solution and is administered orally to the human subject.

9. A method for alleviating the symptoms of, or halting the progression or worsening of the symptoms of cancer, wherein the cancer is selected from the group consisting of gastrointestinal stromal cancer, glioma, melanoma, bladder cancer and renal cancer, comprising administering to a subject having said cancer a sufficient amount of a compound having the formula:

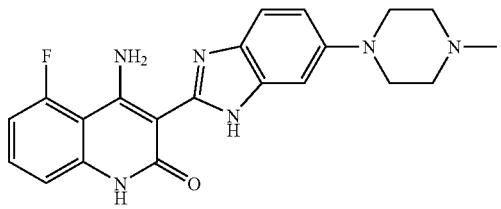

a pharmaceutically acceptable salt thereof, a tautomer thereof, or a pharmaceutically acceptable salt of the tautomer to provide 10 to 2,000 ng/mL of the compound in the subject's plasma 24 hours after administration or 20 to 4,000 ng/mL of the compound in the subject's blood 24 hours after administration.

10. The method of claim 9, wherein the amount of the compound administered is sufficient to provide 20 to 1,000 ng/mL of the compound in the subject's plasma 24 hours after administration or 40 to 2,000 ng/mL of the compound in the subject's blood 24 hours after administration.

11. The method of claim 9, wherein the amount of the compound administered is sufficient to provide 40 to 500 ng/mL of the compound in the subject's plasma 24 hours after administration or 80 to 1,000 ng/mL of the compound in the subject's blood 24 hours after administration.

12. The method of claim 9, wherein the amount of the compound administered is sufficient to provide 40 to 250 ng/mL of the compound in the subject's plasma 24 hours after administration or 80 to 500 ng/mL of the compound in the subject's blood 24 hours after administration.

13. The method of claim 9, wherein the subject is a human.

14. The method of claim 13, wherein the lactate salt of the compound is administered to the subject.

15. The method of claim 14, wherein the lactate salt is in a pill, capsule, tablet, gelcap, caplet, suspension, or aqueous solution and is administered orally to a human subject.

16. The method of claim 9, wherein the compound is administered as a pharmaceutical composition comprising fructose.

17. The method of claim 16, wherein the pharmaceutical composition further comprises a flavoring agent.

18. The method of claim 17, wherein the flavoring agent comprises deterpenated mandarine essential oil.

19. The method of claim 18, wherein the pharmaceutical composition further comprises water.

20. The method of claim 9, further comprising mixing a solid form of the compound with water to form an aqueous mixture before administering the compound to the subject.

21. The method of claim 9, wherein the compound is administered as a pharmaceutical composition selected from granules, powders, suspensions, tablets, pills, capsules, gelcaps, caplets, emulsions, syrups, elixirs, slurries, sprays, aerosols, or solutions.

22. The method of claim 21, wherein the pharmaceutical composition is selected from tablets, pills, capsules, gelcaps, or caplets.

23. The method of claim 9, wherein the compound is administered by injection as a short bolus, slow infusion, or long-term infusion.

24. The method of claim 23, wherein the injection is administered once, twice, three times, or four times daily.

25. The method of claim 9, wherein the amount of the compound administered to the subject ranges from 0.25 to 30 mg/kg body weight of the subject.

26. The method of claim 9, wherein the amount of the compound administered to the subject ranges from 25 to 1500 mg/day.

27. The method of claim 9, wherein the amount of the compound administered to the subject ranges from 200 to 500 mg/day.

28. The method of claim 9, wherein the cancer is selected from the group consisting of gastrointestinal stromal cancer, melanoma, and glioma.

29. The method of claim 9, wherein the cancer is bladder cancer.

30. The method of claim 9, wherein the cancer is renal cancer.

31. The method of claim 9, further comprising administering the compound as part of a treatment cycle, wherein the treatment cycle comprises administering the amount of the compound daily for 7, 14, 21, or 28 days, followed by 7 or 14 days without administration of the compound.

32. The method of claim 31, wherein the treatment cycle comprises administering the amount of the compound daily for 7 days, followed by 7 days without administration of the compound.

33. The method of claim 31, wherein the treatment cycle is repeated one or more times.

34. The method of claim 31, further comprising administering the amount of the compound once, twice, three times, or four times daily during the administration phase of the treatment cycle.

35. The method of claim 9, further comprising administering the amount of the compound once, twice, three times, or four times daily or every other day during a course of treatment.

36. A method for alleviating the symptoms of, or halting the progression or worsening of the symptoms of cancer, wherein the cancer is selected from the group consisting of gastrointestinal stromal cancer, glioma, melanoma, bladder cancer and renal cancer, comprising administering to a subject having said cancer a sufficient amount of a compound having the formula:

a pharmaceutically acceptable salt thereof, a tautomer thereof, or a pharmaceutically acceptable salt of the tautomer to provide an area under the curve (AUC) of 500 to 60,000 ng*h/mL of the compound in the subject's plasma or 750 to 120,000 ng*h/mL of the compound in the subject's blood.

37. The method of claim 36, wherein the AUC is 1,000 to 30,000 ng*h/mL of the compound in the subject's plasma or 1,500 to 60,000 ng*h/mL of the compound in the subject's blood.

38. The method of claim 36, wherein the AUC is 2,000 to 15,000 ng*h/mL of the compound in the subject's plasma or 3,000 to 30,000 ng*h/mL of the compound in the subject's blood.

39. A method for alleviating the symptoms of, or halting the progression or worsening of the symptoms of cancer, wherein the cancer is selected from the group consisting of gastrointestinal stromal cancer, glioma, melanoma, bladder cancer and renal cancer, comprising administering to a subject having said cancer a compound having the formula:

a pharmaceutically acceptable salt thereof, a tautomer thereof, or a pharmaceutically acceptable salt of the tautomer, wherein the amount of compound administered to the subject in a first treatment cycle is 25 mg per day, and the amount of compound administered is increased with each subsequent treatment cycle until either 1500 mg of compound is administered to the subject per day or dose-limiting toxicity is observed in the subject.

40. The method of claim 39 wherein the amount of compound administered is doubled with each subsequent treatment cycle after the first.

41. The method of claim 40 wherein the treatment cycle comprises administering the same amount of the compound daily for 7 days followed by 7 days without administration of the compound.

42. A method for alleviating the symptoms of, or halting the progression or worsening of the symptoms of cancer, wherein the cancer is selected from the group consisting of gastrointestinal stromal cancer, glioma, melanoma, bladder cancer and renal cancer, comprising exposing a human subject having said cancer to an amount of one or more compounds having a formula selected from:

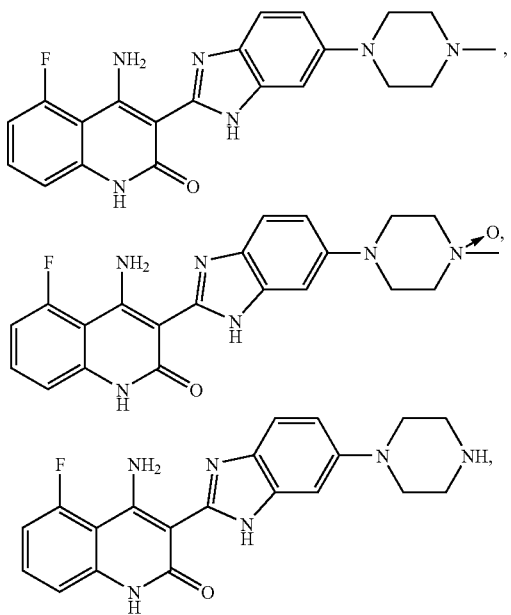

a pharmaceutically acceptable salt thereof, a tautomer thereof, or a pharmaceutically acceptable salt of the tautomer, sufficient to provide a combined $C_{max}$ of 20 to 4000 ng/mL of the one or more compounds in the subject's plasma or a combined $C_{max}$ of 40 to 8000 ng/mL of the one or more compound in the subject's blood.

43. The method of claim 42, wherein the amount of the one or more compounds provides a $C_{max}$ for one of the compounds of 35 to 2600 ng/mL in the subject's plasma or a $C_{max}$ for one of the compounds of 35 to 6000 ng/mL in the subject's blood.

44. The method of claim 42, wherein the amount of the one or more compounds provides a $C_{max}$ for one of the compounds of 35 to 1200 ng/mL in the subject's plasma or a $C_{max}$ for one of the compounds of 50 to 2400 ng/mL in the subject's blood.

45. The method of claim 42, wherein the compound of formula:

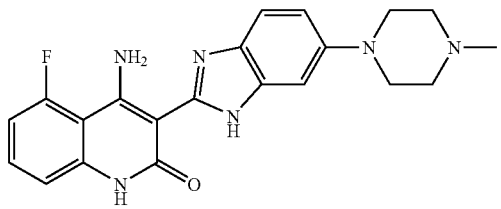

the pharmaceutically acceptable salt thereof, the tautomer thereof, or the pharmaceutically acceptable salt of the tautomer is administered to the subject.

46. The method of claim 42, wherein the compound of formula:

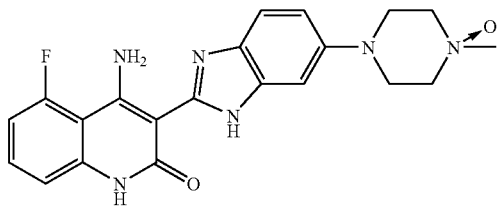

the pharmaceutically acceptable salt thereof, the tautomer thereof, or the pharmaceutically acceptable salt of the tautomer is administered to the subject.

47. The method of claim 42, wherein the compound of formula:

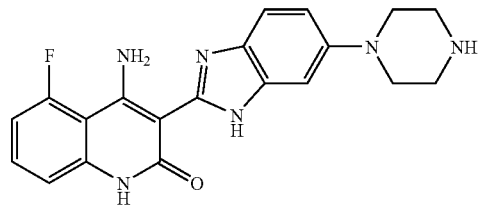

the pharmaceutically acceptable salt thereof, the tautomer thereof, or the pharmaceutically acceptable salt of the tautomer is administered to the subject.

* * * * *